(12) United States Patent
Duty et al.

(10) Patent No.: US 9,196,760 B2
(45) Date of Patent: Nov. 24, 2015

(54) METHODS FOR PRODUCING COMPLEX FILMS, AND FILMS PRODUCED THEREBY

(75) Inventors: Chad E. Duty, Loudon, TN (US); Charlee J C Bennett, Knoxville, TN (US); Ji-Won Moon, Oak Ridge, TN (US); Tommy J. Phelps, Knoxville, TN (US); Craig A. Blue, Knoxville, TN (US); Quanqin Dai, Knoxville, TN (US); Michael Z. Hu, Knoxville, TN (US); Ilia N. Ivanov, Knoxville, TN (US); Gerald E. Jellison, Jr., Oak Ridge, TN (US); Lonnie J. Love, Knoxville, TN (US); Ronald D. Ott, Knoxville, TN (US); Chad M. Parish, Knoxville, TN (US); Steven Walker, Memphis, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 14/110,222

(22) PCT Filed: Mar. 22, 2012

(86) PCT No.: PCT/US2012/030049
§ 371 (c)(1),
(2), (4) Date: Apr. 16, 2014

(87) PCT Pub. No.: WO2012/138480
PCT Pub. Date: Oct. 11, 2012

(65) Prior Publication Data
US 2014/0220724 A1    Aug. 7, 2014

Related U.S. Application Data

(60) Provisional application No. 61/473,385, filed on Apr. 8, 2011, provisional application No. 61/593,394, filed on Feb. 1, 2012.

(51) Int. Cl.
H01L 21/00 (2006.01)
H01L 31/0232 (2014.01)
(Continued)

(52) U.S. Cl.
CPC ............... *H01L 31/0232* (2013.01); *C12P 3/00* (2013.01); *H01L 21/02521* (2013.01);
(Continued)

(58) Field of Classification Search
CPC ................... H01L 21/02521; H01L 21/02568; H01L 21/02601; C12P 3/00
USPC ............ 438/85, 86, 1, 93; 977/932, 936, 952
See application file for complete search history.

(56) References Cited

U.S. PATENT DOCUMENTS
4,027,185 A    5/1977  Nodwell et al.
4,153,201 A    5/1979  Berger et al.
(Continued)

FOREIGN PATENT DOCUMENTS
KR    10-2010-0016544    2/2010
WO    WO 2009/017648 A1   2/2009

OTHER PUBLICATIONS
Bang J.H. et al., "Nanostructured ZnS:$Ni^{2+}$ Photocatalysts Prepared by Ultrasonic Spray Pyrolysis", Adv. Mater. 20:2599-2603 (2008).
(Continued)

*Primary Examiner* — Caridad Everhart
(74) *Attorney, Agent, or Firm* — Scully, Scott, Murphy & Presser, P.C.

(57) ABSTRACT

A method for producing a film, the method comprising melting a layer of precursor particles on a substrate until at least a portion of the melted particles are planarized and merged to produce the film. The invention is also directed to a method for producing a photovoltaic film, the method comprising depositing particles having a photovoltaic or other property onto a substrate, and affixing the particles to the substrate, wherein the particles may or may not be subsequently melted. Also described herein are films produced by these methods, methods for producing a patterned film on a substrate, and methods for producing a multilayer structure.

20 Claims, 7 Drawing Sheets

(51) Int. Cl.
*H01L 21/02* (2006.01)
*C12P 3/00* (2006.01)

(52) U.S. Cl.
CPC ... *H01L 21/02568* (2013.01); *H01L 21/02587* (2013.01); *H01L 21/02601* (2013.01); *H01L 21/02628* (2013.01); *H01L 21/02656* (2013.01)

(56) References Cited

U.S. PATENT DOCUMENTS

| | | | |
|---|---|---|---|
| 4,337,896 A | 7/1982 | Berger et al. | |
| 4,541,564 A | 9/1985 | Berger et al. | |
| 4,700,102 A | 10/1987 | Camm et al. | |
| 4,937,490 A | 6/1990 | Camm et al. | |
| 4,978,067 A | 12/1990 | Berger et al. | |
| 5,219,120 A | 6/1993 | Ehrenberg et al. | |
| 6,080,606 A | 6/2000 | Gleskova et al. | |
| 6,087,196 A | 7/2000 | Sturm et al. | |
| 6,444,453 B1 | 9/2002 | Lauf et al. | |
| 6,506,438 B2 | 1/2003 | Duthaler et al. | |
| 7,060,473 B2 | 6/2006 | Phelps et al. | |
| 7,220,936 B2 | 5/2007 | Ott et al. | |
| 7,365,129 B2 | 4/2008 | Kramer et al. | |
| 7,445,731 B2 | 11/2008 | Okada et al. | |
| 7,572,651 B2 | 8/2009 | Sirringhaus et al. | |
| 7,615,111 B2 | 11/2009 | Oriakhi | |
| 7,655,161 B2 | 2/2010 | Cho et al. | |
| 7,712,680 B2 | 5/2010 | Berger et al. | |
| 8,476,055 B2 * | 7/2013 | Lee et al. | 435/252.1 |
| 2002/0006470 A1 * | 1/2002 | Eberspacher et al. | 427/216 |
| 2004/0079195 A1 * | 4/2004 | Perry et al. | 75/345 |
| 2005/0074511 A1 | 4/2005 | Oriakhi et al. | |
| 2005/0194036 A1 * | 9/2005 | Basol | 136/252 |
| 2006/0121701 A1 * | 6/2006 | Basol | 438/483 |
| 2006/0172168 A1 | 8/2006 | Wright et al. | |
| 2006/0189113 A1 | 8/2006 | Vanheusden et al. | |
| 2006/0211802 A1 | 9/2006 | Asgari | |
| 2007/0108644 A1 | 5/2007 | Cregger | |
| 2007/0110893 A1 | 5/2007 | Lennon et al. | |
| 2007/0163637 A1 * | 7/2007 | Robinson et al. | 136/262 |
| 2007/0163638 A1 | 7/2007 | Van Duren et al. | |
| 2007/0207565 A1 | 9/2007 | Kodas et al. | |
| 2007/0290384 A1 * | 12/2007 | Kodas et al. | 264/5 |
| 2008/0105663 A1 | 5/2008 | Hunt et al. | |
| 2008/0257201 A1 | 10/2008 | Harris et al. | |
| 2009/0139574 A1 | 6/2009 | Pickett et al. | |
| 2009/0246519 A1 * | 10/2009 | Hanson | 428/364 |
| 2009/0274833 A1 * | 11/2009 | Li et al. | 427/123 |
| 2010/0007692 A1 | 1/2010 | Vanmaele et al. | |
| 2010/0065786 A1 | 3/2010 | Simons | |
| 2010/0132507 A1 * | 6/2010 | Perry et al. | 75/345 |
| 2010/0184179 A1 | 7/2010 | Rondinone et al. | |
| 2010/0193752 A1 | 8/2010 | Phelps et al. | |
| 2010/0330367 A1 | 12/2010 | Phelps et al. | |
| 2011/0294254 A1 * | 12/2011 | Jackrel et al. | 438/95 |
| 2012/0164062 A1 * | 6/2012 | Edwards et al. | 423/509 |

OTHER PUBLICATIONS

Dhage S.R. et al., "Rapid Treatment of CIGS Particles by Intense Pulsed Light", *Journal of Physics and Chemistry Solids* 71:1480-1483 (2010).

Dhere N.G. et al., "CIGS2 Thin-Film Solar Cells on Flexible Foils for Space Power", *Progress in Photovoltaics: Research and Applications* 10:407-416 (2002).

Okuyama K. et al., "Technology Innovation in the Nanoparticle Project Synthesis of Nanoparticles and Nanocomposites", *KONA* 25:237-243 (2007).

Song H. et al., "Synthesis and Fluorescence Properties of Pure and Metal-Doped Spherical ZnS Particles from EDTA-Metal Complexes", *Journal of Physics and Chemistry of Solids* 69:153-160 (2008).

Wang W. et al., "Monodisperse, Mesoporous $Zn_xCd_{1-x}S$ Nanoparticles as Stable Visible-Light-Driven Photocatalysts", *J. Phys. Chem. C*. 112(43):16754-16758 (2008).

International Search Report dated Oct. 29, 2012 received from the Korean Intellectual Property Office from Application No. PCT/US2012/030049.

* cited by examiner

```
┌─────────────────────────────────────────────┐
│ Grow Bacterial Culture Suitable for Surviving│
│ Toxicity of Metal or Nonmetal Component      │
└─────────────────────────────────────────────┘
                      ↓
┌─────────────────────────────────────────────┐
│       Provide Source of Nonmetal            │
│         (S, As, Se, and/or Te)              │
└─────────────────────────────────────────────┘
                      ↓
┌─────────────────────────────────────────────┐
│    Incubate Bacterial Culture Suitable for  │
│      Reducing at Least One Nonmetal         │
└─────────────────────────────────────────────┘
                      ↓
┌─────────────────────────────────────────────┐
│        Provide Source of Reducible          │
│                  Metal                       │
└─────────────────────────────────────────────┘
                      ↓
┌─────────────────────────────────────────────┐
│    Incubate Bacterial Culture Suitable       │
│       for Reducing at Least One Metal       │
└─────────────────────────────────────────────┘
                      ↓
┌─────────────────────────────────────────────┐
│       Form Nanoparticle Compound             │
│     Containing Metal and Nonmetal           │
└─────────────────────────────────────────────┘
```

FIG. 1

METHODS FOR PRODUCING COMPLEX FILMS, AND FILMS PRODUCED THEREBY

CROSS REFERENCE TO RELATED APPLICATION

This application claims the benefit of priority from U.S. Provisional Application No. 61/473,385, filed on Apr. 8, 2011 and from U.S. Provisional Application No. 61/593,394, filed on Feb. 1, 2012, the content of which in its entirety is incorporated herein by reference.

This invention was made with government support under Prime Contract No. DE-AC05-00OR22725 awarded by the U.S. Department of Energy. The government has certain rights in the invention.

FIELD OF THE INVENTION

The present invention relates, generally, to the field of film and thin-film deposition, and more particularly, to non-vacuum non-evaporative methods for the production of complex thin films.

BACKGROUND OF THE INVENTION

A significant hindrance encountered in thin film production of complex multi-element compositions is the need to employ a multiplicity of alternating deposition and annealing steps for introducing and reacting each of several elements to produce a single layer in a film. Typically, the deposition step is an evaporative or sputtering method, such as any of the physical and chemical evaporative methods known in the art. Such deposition methods are generally costly, and take much energy and time. Moreover, current deposition methods often employ highly toxic chemicals that are difficult to safely handle, such as the use of hydrogen selenide ($H_2Se$) in a selenization step.

For example, in attempting to deposit a thin film of a photovoltaic composition, such as a copper indium gallium diselenide or copper indium gallium disulfide composition (generally, a CIGs composition), conventional practice has been to deposit one or more metals selected from copper, indium, and gallium, followed by selenization with hydrogen selenide. In other conventional methods, an indium-containing ink is deposited on a substrate, reacted with selenium, and then thermally processed to yield a film having a $In_2Se_3$ composition. After this step, precursors of copper, indium, and gallium inks are combined to form a mixed copper-indium-gallium ink, which is then deposited on the $In_2Se_3$ film before being thermally processed again to provide a CIGs film. As shown, it is not uncommon for current thin film-forming methodologies to take four, five, or more steps, including mixing steps, in depositing such multi-element films.

Furthermore, current thin-film production of complex multi-element compositions is generally not amenable to facile adjustment and optimization of the stoichiometry (i.e., molar ratio) of elements. Nor is current thin-film production of complex multi-element compositions generally known for achieving batch-to-batch repeatability in producing such precise compositions, unless elaborate measures are taken, which are generally not practical for large-scale commercial production.

SUMMARY OF THE INVENTION

In one aspect, the invention is directed to a method for producing a film, wherein the method includes melting a layer of precursor particles having a size of up to 100 microns on a substrate until at least a portion of the melted particles are planarized and merged in said film. In particular embodiments, the method employs a pulse of thermal energy on a layer of particles such that at least a portion of the layer of particles becomes merged (i.e., coalesced) by melting. At least one significant advantage of the instant method over conventional methods of the art is that the instant method is capable of producing films of complex multi-element compositions using only a single precursor deposition step followed by a single film-forming step. In particular embodiments, the instant method achieves this significant advantage by starting with, as a film precursor, a layer of particles having a composition that contains all of the elements to be included in the film. In particular embodiments, the composition of the particles is the same or substantially the same as the composition of the film. A further advantage of the instant method is that, by appropriate refinement or optimization of the composition of the particles, films with precise compositions can be produced, and this, in a repeatable manner and on a commercial scale.

Numerous electronic and photonic devices can benefit from such precise control of the composition and properties of a film. Some of the devices that can benefit from the method described herein include light-emitting diodes (e.g., laser diodes and organoluminescent devices), thin-film batteries, thin-film photovoltaic devices (e.g., thin-film solar cell devices), thin-film semiconductor and electronic devices (e.g., thin-film transistors), thin-film photonic devices (e.g., optoelectronic, photoluminescent, and electroluminescent devices), thin-film display devices, magnetic thin films, magnetoresistive thin films, piezoelectric thin films, thermoelectric thin films, protective thin films, thin-film sensors, thin film catalysts, ferroelectric thin films, solid-state lighting, and thin-film lab-on-a-chip devices. In particular, photovoltaic devices are currently limited by the use of photoluminescent materials that are not tunable, or semi-tunable with great difficulty. Accordingly, the method and film compositions of the invention can greatly advance photovoltaic devices, as well as several other technologies and devices.

In particular embodiments, the method includes subjecting a layer of precursor particles having a size of up to 100 microns to a pulse of thermal energy having an intensity and duration of time effective for melting at least a portion of the precursor particles to produce the film. By the melting process, at least a portion of the particles become planarized and coalesced to form the film. In particular embodiments of the process, the precursor particles have a composition completely or substantially the same as the composition of the film.

In further aspects of the method described above, the invention is directed to non-evaporative, non-vacuum, non-sputtering, non-thermal methods for depositing a layer of particles that functions as the film precursor. In particular embodiments, the method for depositing the layer of particles includes a process that sprays a liquid suspension of the particles. Some particular examples of spray processes considered herein include sonospray and ink-jet spraying. Such deposition processes further simplify and reduce the cost of the process, while also furthering the significant benefits described above, such as producing compositions with precise stoichiometries in a repeatable manner.

In still further aspects of the method described above, the invention is directed to methods for producing the precursor particles, particularly precursor particles having a complex and stoichiometrically precise mixed-element composition. In particular embodiments, the method for producing the particles is a microbially-mediated method. The microbial method can advantageously produce a variety of complex and stoichiometrically-precise mixed-element particle compositions on a commercial (i.e., bulk) scale, while at the same time being substantially cost efficient. In addition, the microbial-mediated method can advantageously produce particles of a particular particle size, morphology, electronic or photonic characteristic, dopant composition, or doping level.

In particular embodiments, the particles produced by the microbial method are non-oxide semiconductor particles, particularly those useful as photovoltaic materials (e.g., particles having a quantum dot, CIGs, or kesterite-type composition), as used, for example, in solar cell devices. A particular advantage of the microbial method is that it provides the capability of synthesizing semiconductor particles having selected photoluminescent characteristics over a wide range of such characteristics. For example, by controlling and/or fine-tuning the size, shape, composition, and/or crystalline structure of the particles, the location or width of the photoluminescence peak can be accordingly controlled or fine-tuned over a wide range.

In particular embodiments, the microbially-mediated method for producing particles includes: (a) subjecting a combination of reaction components to conditions conducive to microbially-mediated formation of multi-element particles (in particular embodiments, non-oxide semiconductor nanoparticles), wherein the combination of reaction components includes i) anaerobic microbes (i.e., "microbes"), ii) a culture medium suitable for sustaining the anaerobic microbes, iii) a metal component (i.e., "metals" or "metal component") that includes at least one type of metal ion to be included in the particle composition, iv) a non-metal (i.e., main group metal) component that combines with the metal component, and v) at least one electron donor that provides donatable electrons to the anaerobic microbes during consumption of the electron donor by the anaerobic microbes; and (b) isolating the particles, which include at least one of the metals and at least one of the non-metals. In particular embodiments, steps (a) and (b) are performed as a single step process.

In one set of embodiments, the precursor particles (and particularly, nanoparticles) have a quantum dot composition, such as CdS, ZnS, CdSe, ZnSe, CdTe, or ZnTe. In another set of embodiments, the precursor particles (and particularly, nanoparticles) have a CIGs-type composition according to the general formula $Cu(In_xGa_{1-x})X_2$, wherein X represents at least one non-metal selected from S, Se, and Te, and x is an integral or non-integral numerical value greater than 0 and less than or equal to 1. In another set of embodiments, the precursor particles (and particularly, nanoparticles) have a kesterite-type composition according to the general formula $M_3SnX_4$, wherein M represents at least one chalcophile metal and X represents at least one non-metal selected from S, Se, and Te.

The invention is also directed to the resulting films produced by the methods described above. The films particularly considered herein have a multi-element composition. In more particular embodiments, the film has a composition that includes at least two or three elements. In even more particular embodiments, the film has a composition wherein at least one or two of the elements is selected from S, Se, Te, P, As, and Sb.

A particular class of films (particularly thin films) considered herein are those possessing a photovoltaic property, i.e., a photovoltaic film or thin film. In more particular embodiments, the photovoltaic film considered herein possesses a metal chalcogenide composition, wherein the chalcogen is at least one element selected from sulfur, selenium, and tellurium, and wherein the film has a thickness up to or below 100, 50, 10, or 5 microns. In even more particular embodiments, the photovoltaic film considered herein has a quantum dot, CIGs, or kesterite-type of composition.

BRIEF DESCRIPTION OF THE DRAWING

FIG. 1. Flow diagram showing a particular embodiment of the microbial-mediated method for preparing metal-chalcogenide particles, and particularly, crystalline nanoparticles.

DETAILED DESCRIPTION OF THE INVENTION

Figure 2:
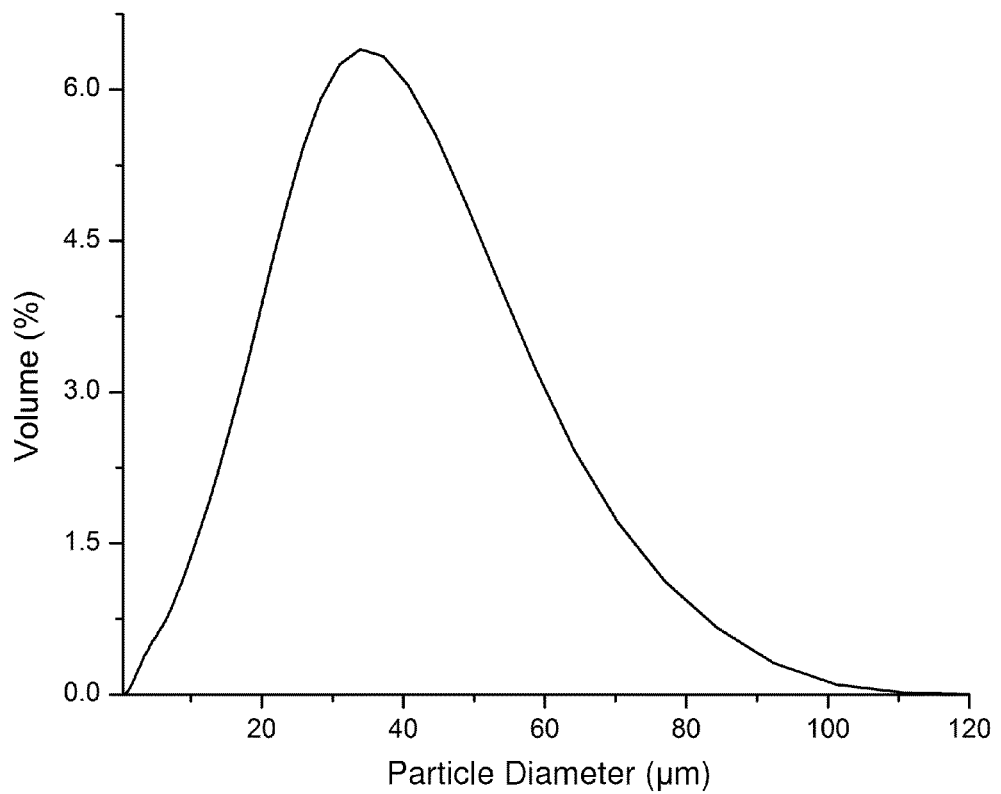
FIG. 2. Graph showing size distribution of as-synthesized CIGs particles (without use of a dispersant) having an average particle size of about 37 μm.

In one aspect, the invention is directed to a method for producing a film from a layer of particles. In some embodiments, the layer of particles can be the film itself, while in other embodiments, the particles in the layer are melted to some degree to form the film. As used herein, the term "layer" can refer to a monolayer, bilayer, trilayer, or higher multi-layer. Moreover, the particles in the layer may be close-packed (i.e., packed as closely as possible) or not close-packed. A monolayer in which the particles are not close-packed can be considered herein to be a sub-monolayer.

In one embodiment, the method produces a film characterized by discrete (i.e., unconnected) particles on a substrate, wherein the particles are affixed to the substrate. By being "affixed" is meant that the particles are made to firmly adhere to the substrate at least strongly enough that they do not separate from the substrate by moderate mechanical action, such as a rinsing or washing step. The particles can be made to firmly adhere by any suitable process, such as a drying, annealing, or chemical bonding step. In some embodiments, the discrete particles in the film are not subjected to a temperature high enough to melt or deform them. In other embodiments, the discrete particles in the film are subjected to a temperature high enough to deform them (i.e., becoming slightly planarized while still being disconnected from each other), or partially melt them so that they become significantly more planarized and may even connect (i.e., consolidate or merge) in places or throughout the film. In some embodiments, the particles in the layer may remain as discrete particles that have become fused together, such as by an annealing or chemical bonding step. Moreover, in some embodiments, the layer of particles that have become fused may be separated from the substrate as a monolithic layer or film of fused particles. For example, a chemical removal step, such as an acidic rinse, may be used to peel off the layer or film of fused particles from the substrate.

In other embodiments, the particles are significantly melted to form a planarized film, which may or may not be porous depending on the extent of melting and areal particle density. The particles can be melted by any suitable process, which can be a pulsed or non-pulsed process. For example, the layer of particles can be melted by heating in a furnace, or by convecting heat through the substrate, such as by a hot plate, or by heating with a dispersed or focused (e.g., laser) form of high-energy electromagnetic radiation, such as infrared, ultraviolet, visible, microwave, x-ray, or radiowave forms of electromagnetic radiation, or by heating with a particle beam (e.g., electron or neutron beam), or by heating with a plasma.

In different embodiments, the electromagnetic radiation used in the non-pulsed or pulsed thermal method can have a wavelength of precisely, about, at least, up to, or less than 0.1 nm, 1 nm, 10 nm, 50 nm, 100 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1050 nm, 1100 nm, 1200 nm, 1300 nm, 1400 nm, 1500 nm, 2000 nm, 2500 nm, 3000 nm, 4000 nm, 5000 nm, 8000 nm, 10 µm, 15 µm, 20 µm, 25 µm, 30 µm, 35 µm, 40 µm, 45 µm, 50 µm, 60 µm, 70 µm, 80 µm, 90 µm, 100 µm, 125 µm, 150 µm, 175 µm, 200 µm, 250 µm, 300 µm, 350 µm, 400 µm, 500 µm, 600 µm, 700 µm, 800 µm, 900 µm, 1 mm, 5 mm, 10 mm, 25 mm, 50 mm, 100 mm, 500 mm, 1 cm, 5 cm, 10 cm, 100 cm, 500 cm, 1 m, 2 m, 5 m, 10 m, 50 m, 100 m, 500 m, or 1000 m, or a wavelength within a range bounded by any two of the foregoing exemplary wavelengths.

In particular embodiments, the invention is directed to a method of forming a film from a layer of particles by melting the layer of particles with a pulse of thermal energy. In the method, a layer of particles (or a portion thereof), wherein the particles typically have a size of up to or less than 100 microns, is melted by a pulse of thermal energy such that at least a portion of the particles in the layer coalesce into a planar form. Particles that coalesce lose their original shape by becoming substantially flattened, while also becoming connected, at least to some extent, with surrounding melted particles. In some embodiments, by suitable choice of particle composition, particle size, pulse power and pulse duration, the particles in the layer merge to form a continuous film (i.e., a film with no voids or pores). In other embodiments, by suitable choice of particle composition, particle size, pulse power and pulse duration, the particles in the layer merge to form a film that contains a degree of porosity. The melting step (i.e., film formation step) described herein is distinct from a sintering, annealing, or crystallographic phase transformation step, since the foregoing types of processes alter properties or characteristics of a material without melting the material.

The pulse thermal method considered herein can be any method that can subject a layer of particles to a pulse of intense thermal (i.e., radiant) energy. Generally, the means by which the radiant energy is produced does not substantially alter or degrade the composition of the particles. In particular embodiments, the radiant pulse is provided by an intense pulse of electromagnetic radiation. To produce heat in a material, the electromagnetic radiation is generally absorbed by the material and emitted as thermal energy.

The film formation step can employ any temperature above the melting point of the particles to be melted into a film. The melting point of the particles (particularly in the case of nanoparticles) may be significantly less than that of the corresponding bulk material due to the energy inherent in particles. Thus, the temperature of the non-pulsed heating step or thermal pulse can widely vary depending on the composition of the particles. In some embodiments, the non-pulsed heating step or thermal pulse employs a temperature of precisely or about the melting point of the particles to be melted (for example, at, or up to five degrees Celsius above the melting point). In other embodiments, the non-pulsed heating step or thermal pulse provides a temperature substantially above the melting point of the particles to be melted, such as a temperature of 10, 25, 50, 75, 100, 125, 150, 200, 250, 300, 350, 400, 450, or 500 degrees Celsius (° C.) above the melting point of the particles to be melted. However, it is generally preferred that the temperature generated by the non-pulsed heating step or thermal pulse is lower than a decomposition temperature of the material being melted, although a temperature higher than a decomposition temperature may be used if a small enough pulse duration is employed to prevent or substantially minimize the decomposition, or in the case of a non-pulsed heating step, conditions (e.g., atmosphere composition and pressure) can be selected to minimize or prevent decomposition. In other embodiments, the temperature of the non-pulsed heating step or thermal pulse is high enough to cause melting along with a compositional conversion if such final composition is desired (e.g., heating of metallic particles in the presence of oxygen to form the metal oxide).

In the particular case of metal chalcogenide compositions, including quantum dot, CIGs, and kesterite-type compositions, the non-pulsed heating step or thermal pulse preferably employs a temperature of at least 800° C., 850° C., 900° C., 950° C., 1000° C., 1050° C., 1100° C., 1150° C., 1200° C., 1250° C., 1300° C., 1350° C., 1400° C., 1450° C., 1500° C., 1550° C., 1600° C., 1650° C., 1700° C., 1750° C., 1800° C., 1850° C., 1900° C., 1950° C., 2000° C., 2100° C., or 2200° C. The temperature may also be within a range bounded by any two of the foregoing exemplary temperatures, or alternatively, precisely, up to, less than, at least, or above any of the foregoing exemplary temperatures, wherein the term "about", used for the temperature, generally indicates within ±5, ±4, ±3, ±2, or ±1° C. of the indicated temperature. The term "about" may also be used herein, generally, to indicate ±10%, ±5%, ±2%, or ±1% of a value.

In the pulsed version of the method, one or more pulses are applied to the layer of precursor particles (i.e., particles in the precursor layer) to achieve melting and film formation of the particles. In one embodiment, a single pulse achieves melting and film formation of the particles in the precursor layer. In another embodiment, more than one pulse (e.g., two, three, or a multiplicity of pulses), separated by a time interval between pulses, achieves melting and film formation of the precursor particles. The pulse duration of each pulse can widely vary depending on such factors as the absorbing ability of the particles, the particle size, the wavelength of light, the temperature, and substrate (underlying layers) used. It is understood that a longer pulse duration generally results in a higher applied temperature. In particular embodiments, the stoichiometry of elements in each particle of the precursor layer is the same as the stoichiometry of elements in the final film.

Generally, the pulse duration is no more than 10, 5, or 1 second, and more typically, 100-500 milliseconds (ms). In different embodiments, the pulse duration can be precisely, about, at least, up to, or less than, for example, 1 second (i.e., 1000 ms), 500 ms, 400 ms, 300 ms, 200 ms, 100 ms, 50 ms, 20 ms, 10 ms, 5 ms, 1 ms (i.e., 1000 microseconds, i.e., 1000 µs), 900 µs, 800 µs, 700 µs, 600 µs, 500 µs, 400 µs, 300 µs, 200 µs, 100 µs, 80 µs, 50 µs, 40 µs, 30 µs, 20 µs, 10 µs, 5 µs, 2.5 µs, 1 µs, 0.5 µs, 0.25 µs, or 0.1 µs, or a pulse duration within a range bounded by any of the foregoing exemplary values. In different embodiments, the pulse energy can be, precisely, about, at least, up to, or less than, for example, 1, 2, 5, 10, 25, 50, 100, 200, 300, 400, 500, 600, 700, 800, 900, or 1000 J/cm². As known in the art, a pulse power (i.e., in W/cm²) can be derived by dividing the pulse energy (i.e., in J/cm²) by the pulse duration (in seconds).

If multiple pulses are used, the pulse duration may be the same or the pulse duration may vary across different pulses. For example, in different embodiments, the pulse duration alternates, or successively increases or decreases with time. When multiple pulses are used, the time interval between pulses (i.e., the periodicity) can also be appropriately selected. In different embodiments, the time interval is maintained below the pulse duration, maintained above the pulse duration, or increased or decreased with time successively or in a pattern-wise manner. The time interval can be, for example, precisely, about, at least, up to, or less than, for example, any of the exemplary values provided above for pulse duration, typically no more than about 1 or 2 seconds. The time interval may also be within a range bounded by any of the aforesaid values and/or any of the values provided above for pulse duration. The frequency of the pulses can be precisely, about, at least, up to, or less than, for example, 1 min$^{-1}$, 10 min$^{-1}$, 20 min$^{-1}$, 30 min$^{-1}$, 40 min$^{-1}$, 50 min$^{-1}$, 1 sec$^{-1}$ (1 Hz), 5 sec$^{-1}$, 10 sec$^{-1}$, 20 sec$^{-1}$, 30 sec$^{-1}$, 40 sec$^{-1}$, 50 sec$^{-1}$, 100 sec$^{-1}$, 500 sec$^{-1}$, 1000 sec$^{-1}$, 5000 sec$^{-1}$, 1×10$^4$ sec$^{-1}$, 5×10$^4$ sec$^{-1}$, 1×10$^5$ sec$^{-1}$, 5×10$^5$ sec$^{-1}$, 1×10$^6$ sec$^{-1}$, 5×10$^6$ sec$^{-1}$, 1×10$^7$ sec$^{-1}$, or 5×10$^7$ sec$^{-1}$, or a frequency within a range bounded by any of the foregoing exemplary values.

The pulse of electromagnetic radiation may be suitably adjusted in several other ways. For example, the pulse of electromagnetic radiation can be suitably adjusted, by means well known in the art, in its amplitude, phase, and extent of collimation. Collimation can be achieved by, for example, use of a collimator, such as a collimation lens or parabolic or spherical mirrors. Substantially collimated light corresponds to a laser emission, which is also considered herein as the pulse of electromagnetic radiation. The spectrum of the impinging radiation may also be appropriately filtered to provide particular wavelengths or a narrowed range of wavelengths.

The pulse of electromagnetic radiation can also be suitably adjusted in its power (i.e. intensity). The intensity of the pulse of electromagnetic radiation is generally at least 100 W/cm². In different embodiments, the pulse of electromagnetic radiation can be precisely, about, at least, or above, for example, 100, 200, 500, 1000, 2000, 3000, 4000, 5000, 6000, 7000, 8000, 9000, 1×10$^4$, 1.5×10$^4$, 2×10$^4$, 2.5×10$^4$, 3×10$^4$, 3.5×10$^4$, 4×10$^4$, 4.5×10$^4$, 5×10$^4$, 5.5×10$^4$, 6×10$^4$, 6.5×10$^4$, 7×10$^4$, 7.5×10$^4$, 8×10$^4$, 9×10$^4$, or 1×10$^5$ W/cm², or an intensity within a range bounded by any of the foregoing exemplary values.

In particular embodiments, the pulsed thermal method employs a stabilized plasma arc high intensity radiation source, as described, for example, in U.S. Pat. Nos. 4,027,185 and 4,700,102, the contents of which are incorporated herein by reference in their entirety. As described in said patents, the arc can be suitably restricted by use of a vortexing liquid wall. Numerous modifications and improvements of the plasma arc method are known. For example, the instant invention incorporates by reference the contents of U.S. Pat. No. 4,937,490, which describes a high intensity radiation arc apparatus that includes liquid injecting means, gas injecting means, and exhausting means in the arc chamber in order to provide a liquid vortex motion and a gas vortex motion to restrict the plasma arc. Further adjustments, modifications, and optimizations of the processes and apparatuses taught in the foregoing patents can be made to better conform with the aims and goals of the instant invention, as described above. For example, the processes and apparatuses taught in the foregoing patents can be configured to emit a high intensity of electromagnetic radiation, particularly of the infrared wavelengths. Other modifications not contemplated in said foregoing patents may also be necessary to make the arc plasma systems described therein capable of operating within the parameters described herein, e.g., to provide any of the particular pulse durations, frequencies, power, or wavelengths described above. In particular embodiments, the thermal pulse method described herein utilizes a plasma arc lamp with an argon plasma. The use of a plasma arc lamp with an argon plasma provides the particular advantage of providing a significantly increased operating space compared to other thermal pulse configurations of the art, such as those using a flash lamp, particularly a xenon flash lamp.

Other methods for applying a thermal pulse are considered herein. For example, in some embodiments, a rapid physical heating process, such as by use of a heated resistor filament or other heated element in proximity to the layer of particles, can be utilized. In such a heating process, a capacitor may be employed for storing and releasing a large amount of electrical energy to the heating element, thereby generating a quick pulse of thermal energy. In other embodiments, a pulse of direct or alternating current may be applied to the substrate. By appropriate selection of such characteristics as current level, amplitude, and frequency, the pulse of current can be adjusted to melt at least a portion of the layer of precursor particles. The frequency of the alternating current can be any suitable frequency, particularly a radiofrequency. Some types of particles, such as the iron oxides and certain ferrites, are known to have a thermomagnetic ability. Thus, in other embodiments, a magnetic pulse can be employed for heating a layer of precursor particles, if such particles are susceptible to a thermal increase upon exposure to a strong magnetic field. In yet other embodiments, one or more of any of the means, described above, for generating a thermal pulse is excluded from the method described herein. In still other embodiments, a combination of any of the heating means described above is used in the film-forming method described herein.

In some embodiments, particularly where the precursor nanoparticles are not substantially susceptible to oxidation, the non-pulsed or pulsed thermal methods described above can be conducted in air. In other embodiments, air oxidation may be desired, e.g., in the production of an oxide composition. To promote oxidation, an elevated oxygen atmosphere may be employed. However, in other embodiments, particularly in situations where the precursor nanoparticles are susceptible to oxidation, or where oxidation or oxygen incorporation is not desired, an inert atmosphere may be employed. The inert atmosphere may include, or be a mixture of, or be composed solely of, for example, nitrogen, or a noble gas, such as helium, neon, or argon. In some embodiments, hydrogen gas may be included in the process in order to chemically reduce the film. Yet other chemical environments may also be used for reacting the film in different ways. For example, in some embodiments, a sulfur (S), selenium (Se), or tellurium (Te) species (e.g., $H_2S$, $H_2Se$, or $H_2Te$, or an organic derivative thereof) may be incorporated into the atmosphere in order to maintain or increase the amount of S, Se, or Te in the film.

The method described herein can advantageously produce a porous film. By adjusting such variables as the time duration and temperature of the thermal pulse, the level of porosity can be adjusted. Other variables, such as the size of the precursor particles, their melting points, as well as the average distance between particles (i.e., particle interspacing), can also be adjusted in order to adjust the degree of porosity. Longer pulse times allow the precursor particles more time to flatten (i.e., planarize) during the melting process. The longer the period of time that the precursor particles are afforded to planarize, the greater the surface area covered by the melted particles, and hence, the less porous and more continuous the film. Generally, when a sufficient surface concentration of particles is provided, complete melting and planarization results in a continuous film. However, the thermal pulse can be sufficiently shortened to an extent that the particles are not provided sufficient time to completely planarize. In such a case, the particles will generally flatten and interconnect with each other, while leaving some open spaces (i.e., pores). The pores considered herein can be, for example, spaces of exposed substrate or an exposed underlying layer, or simply voids in the film plane. The larger the particle size, the lower the tendency to melt and planarize, and thus, particle size can also be used to appropriately adjust the porosity of the film. Since larger particle interspacing decreases the amount of particle-particle merging during planarization, adjustments in particle interspacing can also be used to appropriately adjust the porosity of the film. In turn, particle interspacing can be adjusted by, for example, adjusting the surface concentration of particles on the substrate or by use of particle-separating molecules (molecular spacers) or a framework template.

The method can also include any useful additional step before deposition of the precursor particles, or after deposition of the precursor particles and before the non-pulsed or pulsed thermal method (i.e., an intermediate step), or after production of the film. Some possible additional steps before deposition of the precursor particles include preparation of a thin film of the substrate, or modification of a bulk or thin-film substrate material to include a thin film thereon before deposition of the particles, or modification of a substrate surface by imprinting or embedding a pattern thereon that produces a corresponding pattern in the layer of particles. Some possible intermediate steps include a drying step (of the layer of precursor particles), an annealing step, a magnetic alignment step, the deposition of one or more chemicals on the layer of particles (e.g., to affix the particles onto the substrate), or the reaction of the layer of particles with one or more chemicals (to, for example, modify the composition of the particles, or to etch portions of the layer of particles), or to include patterning means (e.g., a patterning mask) in order to produce a pattern in the resulting film. Some possible additional steps after producing the film include a heating step (wherein the temperature used in the heating step is generally lower than the temperature used in the non-pulsed or pulsed thermal method, e.g., an annealing step), or deposition of one or more topcoats or intermediate thin films, deposited by methods described herein or by any methods known in the art (e.g., lithographic, photolithographic, sputtering, CVD, or PVD methods known in the art).

The resulting film has a thickness generally up to or less than 100 microns (100 μm), or a thickness corresponding to any of the particle sizes herein provided. In different embodiments, the film has a thickness of precisely, about, up to, or less than, for example, 100 μm, 50 μm, 25 μm, 10 μm, 5 μm, 2 μm, 1 μm, 500 nm, 400 nm, 300 nm, 200 nm, 100 nm, 75 nm, 50 nm, 25 nm, 20 nm, 15 nm, 10 nm, 5 nm, 4 nm, 3 nm, 2 nm, or 1 nm, or a thickness within a range bounded by any two of the foregoing values. Although the foregoing values are intended to correspond to a single thin film (i.e., a single layer), any of the foregoing values may also correspond to the thickness of a multilayer structure (i.e., a structure containing a multiplicity of films, generally in a stacked arrangement). Since the thickness of each layer in a multilayer film may be selected from any of the foregoing exemplary thicknesses, it is possible, in some embodiments, for a multilayer structure to have a thickness over 100 μm, such as precisely, about, up to, or less than, for example, 200 μm, 300 μm, 400 μm, 500 μm, or 1 mm. In other embodiments, a single film and/or the particles deposited on the substrate can have a thickness or diameter, respectively, corresponding to any of the exemplary larger thicknesses provided above for a multilayer structure. Moreover, one skilled in the art will recognize that, although a planarized film is generally not thinner than the maximum sized particles, it is possible for the film to be thinner than a particle diameter in instances where the packing density is sufficiently low.

In some embodiments, the resulting film is continuous. A continuous film, as considered herein, does not contain pores (i.e., has a 0% degree of porosity) or spacings between deposited particles whether in melted or unmelted form. In other embodiments, the film is constructed of melted and merged particles, except that the film includes a degree of porosity (i.e., spaces or pores surrounded by melted and merged particles). In different embodiments, the degree of porosity is precisely, about, at least, up to, or less than 5%, 10%, 20%, 30%, 40%, 50%, 60%, 70%, or 80% by surface area of the film, or within a range bounded by any two of the foregoing exemplary values. In particular embodiments, the film contains an ordered (i.e., uniform or patterned) distribution of pores. Porous films, and ordered porous films in particular, are of significant interest in numerous specialized applications, such as catalysis, low dielectric constant materials, photonics, and separation media (e.g., chromatography). The pores can be, for example, nanopores, mesopores, micropores, macropores, or a combination thereof. In other embodiments, the pores can have any of the exemplary sizes provided hereinbelow for the precursor particles.

The particles considered herein can have any suitable size, although, generally, the particle size considered herein is no more than about 100 μm. In different embodiments, the particle size is precisely, about, up to, or less than, for example, 100 μm, 50 μm, 25 μm, 10 μm, 5 μm, 2 μm, 1 μm, 500 nm, 400 nm, 300 nm, 200 nm, 100 nm, 75 nm, 50 nm, 25 nm, 20 nm, 15 nm, 10 nm, 5 nm, 4 nm, 3 nm, 2 nm, or 1 nm, or a size within a range bounded by any two of the foregoing values. The exemplary particle sizes provided above can refer to a primary crystallite size or an agglomerate. The primary crystallite size particularly considered herein is a size up to or less than 50 μm, more typically up to or less than 10 μm, more typically up to or less than about 1 μm, more typically up to or less than about 500 nm or 100 nm, and even more typically in the range of 50-75 nm or 50-100 nm. Agglomerates generally have a size of at least 500 nm or 1 μm and up to 10, 20, 50, or 100 μm, but can be significantly larger (e.g., up to, less than, or greater than 200 μm, 300 μm, 400 μm, 500 μm, 600 μm, 700 μm, 800 μm, 900 μm, or 1000 μm) depending on the extent of agglomeration or size of the primary crystallite. For substantially symmetrical particles, such as spherical or cubic particles, the foregoing exemplary sizes correspond to a diameter or the length of all dimensional axes. However, for particles that have dimensional axes of substantially different size (e.g., oval, rectangular, or rod-like), the indicated size may be an average size (e.g., based on a sphere having an equivalent volume). Alternatively, the size of the particle may be described by each of its dimensional axes, i.e., one, two, or three of the dimensional axes of the particles may be selected from the exemplary sizes provided above (or within a range therein), or the particles may contain one or two dimensional axes selected from the exemplary sizes provided above, while the one or two remaining dimensional axes have a larger size (e.g., about, up to, or at least 200 µm, 300 µm, 400 µm, 500 µm, or 1 mm in length).

In particular embodiments, the primary or aggregate particles have a size (i.e., "diameter" for spherical or polyhedral nanoparticles) in the nanoscale regime, i.e., less than 1 micron (1 µm). In different embodiments, the nanoparticles can have at least one dimension of at least 1 nm, 2 nm, 3 nm, 4 nm, 5 nm, 10 nm, 12 nm, 15 nm, 20 nm, 25 nm, 30 nm, 40 nm, 50 nm, 100 nm, 150 nm, 200 nm, 250 nm, 300 nm, 400 nm, or 500 nm, or any range therebetween, or a size within a range bounded by any of the foregoing values (e.g., 1-10 nm, 2-10 nm, 1-20 nm, 2-20 nm, 3-20 nm, 1-500 nm, 5-500 nm, 1-150 nm, or 5-150 nm). In one embodiment, the particles are fairly disperse in size (e.g., having a size variation of up to 20%, 30%, 40%, 50%, or greater from a median or mean size). In another embodiment, the particles are fairly monodisperse in size (e.g., having a size variation of, up to, or less than 10%, 5%, 2%, or 1% from a median or mean size).

In some embodiments, the size of the particles is selected to adjust a grain size in the film. For example, use of nanoparticles can produce nanosized grains in the corresponding film. Different applications can benefit by careful adjustment of the grain size.

The particles considered herein can have any composition that can be used in preparing a useful film in accordance with the method described above. For example, the particles can have an organic or inorganic composition. In some embodiments, the particles are composed of a single element. In other embodiments, the particles are multi-elemental by being composed of, for example, two, three, four, or a greater number of elements.

In some embodiments, multi-element particles having a substantially or completely uniform composition with a precise stoichiometric ratio between elements are converted, by the non-pulsed or pulsed thermal methods described herein, to a film containing the same or substantially the same composition with the same or substantially the same stoichiometric ratio between elements as found in the precursor particles. By being "substantially the same" with respect to composition and stoichiometric ratio is meant that the film contains all of the elements found in the precursor particles and in a stoichiometric ratio that diverges by no more than, generally, about 25% (or 20%, 10%, 5%, 2%, or 1%) of the stoichiometric ratio found in the precursor particles. In the foregoing embodiment, the composition of the film can be adjusted and fine-tuned by corresponding adjustment and tuning of the composition and stoichiometric ratio between elements in the precursor particles.

In other embodiments, multi-element particles having a substantially or completely uniform composition with a precise stoichiometric ratio between elements are converted, by the non-pulsed or pulsed thermal methods described herein, to a film containing a substantially different composition or a substantially different stoichiometric ratio between elements as found in the precursor particles. The difference in composition or stoichiometric ratio is generally a result of the conditions employed in the method. For example, a thermal pulse may, in some cases, vaporize or chemically alter a portion of one or more elements in the precursor particles. In such situations, the altering effects of the thermal pulse may be compensated by appropriate adjustment of the precursor particles. For example, if the thermal pulse, under specified conditions, is known to remove a specified portion of an element (for example, selenium), precursor particles containing the requisite excess amount of the element can be prepared to produce a film having a desired composition. The excess amount may be, for example, at least 5%, 10%, 20%, 30%, 40%, 50%, 60%, 70%, 80%, 90%, 100%, 120%, 150%, or 200% of one or more elements. In the foregoing embodiment, the composition of the film can be adjusted and fine-tuned by corresponding adjustment and tuning of the composition and stoichiometric ratio between elements in the precursor particles.

The layer of particles can also include a mixture of different types of particles. The particles can be different in, for example, composition or size. By having different types of particles, the particles are not uniform. However, in some embodiments, different sets of particles are each uniform with respect to an attribute, such as composition, shape, and/or size, but each set is different from the other in at least one other attribute. A mixture of particles can be used, for example, in making functionally graded materials, as well as in additive manufacturing, particularly where some materials are included as a sacrificial support structure.

In one embodiment, the particles differ in size. For example, nanoparticles may be used in combination with microparticles or macroparticles. At least one possible benefit in using a combination of particle sizes is the tendency of such combinations to produce an ordered arrangement of particles, which may produce a more structurally-ordered film. A combination of particle sizes can also, in some cases, cause a more disordered arrangement, which may produce a more disordered (or amorphous) film. A combination of particle sizes may also decrease porosity, which may result in a more compact film.

In other embodiments, the particles differ in composition, and may have the same (i.e., uniform) or different sizes. Particles of different compositions can be beneficial in several embodiments. For example, in embodiments where an excess of one or more elements is desired, the excess can be incorporated as separate particles (for example, a combination of CIGs (selenide) and Se-containing particles may be used to produce a CIGs film containing a desired amount of Se). As another example, while particles of uniform composition generally produce a homogeneous film, a mixture of particle compositions can be advantageous in producing a heterogeneous film (i.e., that contains areas differing in composition, generally in a uniformly patterned manner, or depth differing in gradual change in composition with the same phase). Such heterogeneous films may advantageously provide a multifunctional film, i.e., with two or more distinct properties, such as a sensing portion and a light-emitting portion, or first and second light-emitting portions with different light-absorbing and/or light-emitting functions or characteristics.

In some embodiments, the layer of particles contains only particles, while in other embodiments, the particles in the layer are mixed or contacted with one or more non-particulate substances. The non-particulate substances can be, for example, liquid or gaseous forms of additional precursor chemicals. In some embodiments, the liquid is a liquid medium (e.g., aqueous or organic solvent) within which particles are suspended during the process in which the particles are deposited on a substrate. In particular embodiments, the liquid medium includes one or more additional precursor chemicals.

In some embodiments, the particles in the layer are not stacked, i.e., the layer is a monolayer of particles. In the monolayer of particles, the particles can be contiguous, or alternatively, there can be a spacing between particles. The spacing between particles can be occupied by other types of particles, non-particle precursors, a liquid or gaseous medium or matrix (which can be sacrificial), chemical spacers, or void space (e.g., fillable by a gas or vacuum). In other embodiments, the particles in the layer, or a portion thereof, are stacked. The stacking can be, for example, a bilayer, trilayer, or higher multilayer of particles (e.g., tens or hundreds of stacked particles).

The method described herein may also include the manner in which the layer of particles is formed. Any method known in the art for producing a layer of particles is applicable herein. The method can, for example, employ any of the physical and/or chemical methods (e.g., PVD, CVD, or CBD) described above for depositing particles onto a substrate.

In particular embodiments, the layer of particles is formed by spraying a liquid suspension of the particles onto a substrate. The suspension of particles can be prepared by suspending (e.g., by mixing) a portion of particles into a liquid matrix that does not dissolve or adversely react with the particles. The liquid matrix can be, for example, aqueous (e.g., water or a water-solvent mixture) or one or more organic solvents, such as one or more of an alcohol, ether, alkylhalide, sulfoxide, amide, ketone, or nitrile solvent.

A particular spraying method considered herein for depositing particles on a substrate is the sonospray method. The sonospray method is described in detail in, for example, U.S. Pat. Nos. 4,153,201, 4,337,896, 4,541,564, 4,978,067, 5,219,120, and 7,712,680, the contents of which are herein incorporated by reference in their entirety. The sonospray method is a non-vacuum deposition method amenable to the manufacture of large area films, along with low processing costs. In brief, the sonospray method employs an ultrasonic nozzle that operates by use of a piezoelectric transducer that produces a high frequency motion when subjected to a high frequency electrical signal. The high frequency vibration produced by the piezoelectric material travels down a horn of the nozzle. Liquid emerging from the surface of the horn is broken into a fine spray, which is highly controllable with respect to droplet size and distribution. As detailed in J. Kester, et al., CP394, NREL/SNL PV Prog. Rev., pp. 162-169, AIP Press, NY, 1997, the sonospray approach has been used to produce a CdTe thin film. The contents of the foregoing reference are also herein incorporated by reference in their entirety.

Another particular spraying method considered herein for depositing particles on a substrate employs ink-jet spraying, and in particular embodiments, ink-jet spraying with multiple ink-jet heads for spraying a multiplicity of different particle compositions. Ink-jet spraying methods, particularly as used in producing patterned surfaces, are described in detail in, for example, U.S. Pat. Nos. 7,572,651, 6,506,438, 6,087,196, 6,080,606, 7,615,111, 7,655,161, and 7,445,731, the contents of which are incorporated herein by reference in their entirety.

The substrate on which the precursor particles reside can be any useful substrate known in the art, including functional substrates and sacrificial substrates. The choice of functional substrate is very much dependent on the application or end-use. For many applications, the substrate can be selected from, for example, a metal (e.g., Co, Ni, Cu, Zn, Pt, Au, Ru, Mo, W, Ta, or Rh, stainless steel, a metal alloy, or combination thereof), a metal oxide (e.g., glass or a ceramic material, such as F-doped indium tin oxide), a metal nitride (e.g., TaN), a metal carbide, a metal silicide, a metal boride, a rigid or flexible plastic or polymer film, or a combination thereof, or multilayer composite thereof. Some of these substrates, such as molybdenum-coated glass and flexible plastic or polymeric film, are particularly considered herein for use in photovoltaic applications. The photovoltaic substrate can be, for example, an absorber layer, emitter layer, or transmitter layer useful in a photovoltaic device. Other of these substrates can be used as dielectric or conductive layers in a semiconductor assembly device. Still other of these substrates (e.g., W, Ta, and TaN) may be useful as copper diffusion barrier layers, as particularly used in semiconductor manufacturing. The method described herein is particularly advantageous in that it can be practiced on a variety of heat-sensitive substrates (e.g., low-temperature plastic films) without damaging the substrate.

In some embodiments, the particles can be bound onto the substrate surface by, for example, covalent, ionic, hydrogen, and/or dative bonds such that they are affixed to the substrate. In embodiments where the particles are to be melted, the particles may, at first, reside on the substrate surface without being bound to the substrate; generally, the melting process affixes the melted particle composition to the substrate. In yet other embodiments, the particles are embedded to some degree in the substrate surface while being sufficiently accessible for conversion to a film in accordance with the non-pulsed or pulsed thermal methods described herein.

In some embodiments, the film described herein has a single (i.e., uniform) composition within the film. However, in other embodiments, the film has two or more (i.e., a multiplicity) of compositions within the film. The multiplicity of compositions in the film can be patterned, or, in some embodiments, different compositions within the film describe particular shapes, such as circuit paths or other electrically- or photonically-useful shapes or patterns, including those used in semiconductor devices. At least one method contemplated herein for producing a multi-compositional film relies, at least in part, on ink-jet printing of particles of the same or different compositions, deposited on a substrate in a specific arrangement, i.e., in a pattern-wise manner. In particular embodiments, at least two different types of particles are deposited by ink-jet printing to produce a pattern in which the different types of particles are in separate regions of the pattern.

Other techniques, such as masking, can also be used in producing a variety of useful shapes. For example, a uniform layer of a first set of particles having a first composition can be overlaid by a mask that protects a portion of the particles from being converted to a film by the pulse method described herein. Subsequent washing and/or ablation techniques can be used to remove unexposed areas. In other embodiments, either after or in lieu of a washing and/or ablation step, a second set of particles having a second composition can be overlaid on a portion of, or the entire area of, the first layer of particles. The second layer of particles, or a portion thereof, can be similarly converted to a film or patterned layer. Additional particle layers can be added, with optional masking during film conversion, to produce intricate multilayer structures. In yet other embodiments, a masking technique is used during deposition of particles onto a substrate to produce a specific shape or pattern of the precursor particle layer. The pattern is translated into the resulting film by application of the pulsed thermal method described herein. In other embodiments, a pulse laser scribing method, as known in the art, with or without a mask, may be employed herein to produce a pattern from the layer of precursor particles.

A multilayer structure can be produced by any of the techniques described above. In some embodiments, the multilayer structure contains only films of uniform composition. In other embodiments, the multilayer structure contains one, two, or more films that are non-uniform in composition. One or more of the individual films in the multilayer structure can have intricate or patterned shapes to make them useful for any of a variety of end-applications. Complex three-dimensional structures can be built by the sequential deposition and film production process described above.

In a first set of embodiments, a multilayer structure is produced by: (i) subjecting a select portion of a first layer of precursor particles to a pattern-wise pulse of thermal energy that pattern-wise (e.g., via a mask or scribing technology) melts the select portion of precursor particles to an extent that the melted particles are planarized and merged to produce a pattern in the first layer; (ii) depositing a second layer of precursor particles on the first patterned layer; and (iii) subjecting at least a portion of the second layer of precursor particles to a pulse of thermal energy to melt at least a portion of the second layer of precursor particles to an extent that the melted particles are planarized and merged.

In a second set of embodiments, a multilayer structure is produced by: (i) producing a patterned layer of precursor particles (e.g., by ink-jet printing or sonospray techniques); (ii) subjecting the patterned layer of precursor particles to a non-pulsed or pulsed form of thermal energy that melts the precursor particles to an extent that the melted particles are planarized and merged to form a patterned first layer; (iii) depositing a second layer of precursor particles on the patterned first layer; and (iv) subjecting at least a portion of the second layer of precursor particles to a non-pulsed or pulsed form of thermal energy to melt at least a portion of the second layer of precursor particles to an extent that the melted particles are planarized and merged.

Depending on the desired end application, the second or higher layer of precursor particles in the embodiments described above may or may not also be patterned. In other embodiments, a first layer is not patterned (e.g., to function as a base substrate), while the second layer may or may not be patterned, depending on the desired end application. Trilayer and higher multilayer structures may be produced by further iterations of the deposition and pulse steps described in the above exemplary embodiments. In some embodiments, a single or multilayer structure is produced by combining the first and second sets of embodiments described above, i.e., by patterning of precursor particles (e.g., by ink-jet printing) in addition to pattern-wise pulsing, such as by mask or scribing techniques.

Non-uniform portions of a multi-compositional film may, in some embodiments, not differ in composition, but rather, in a physical characteristic, such as degree of porosity, density, phase, or film thickness. The non-uniform portions may also differ both in composition and a physical characteristic. Likewise, individual films in a multilayer structure may, in some embodiments, not differ in composition while differing in a physical characteristic. A film containing a difference in physical characteristics can be produced by, for example, masking techniques in which a first portion of the precursor particles are subjected to a first set of pulse thermal conditions and a second portion of the precursor particles are subjected to a second set of pulse thermal conditions, wherein the difference in first and second sets of pulse thermal conditions causes the physical difference in resulting first and second portions of the film. In particular embodiments, a film produced by the pulse thermal method described herein possesses a gradation in any of the physical characteristics described above. For example, the film may possess a gradation in the degree of porosity from one location of the film to another location. In other embodiments, individual films in a multilayer structure possess a gradation in any of the physical characteristics described above, i.e., from one film to the next in the multilayer structure. For example, individual films in a multilayer structure may gradually change in porosity level from the film closest to the substrate to the film farthest from the substrate.

In a first set of embodiments, the particles considered herein (and/or the resulting film), or a portion thereof, have an organic composition. It is understood that all of the precursor particle compositions described in this application are also contemplated as compositions of the resulting film. For the purposes of this application, an organic composition is one containing carbon, either in compound or elemental form. Numerous applications exist for carbon-containing films. Some of these include protective or barrier films in the case of organic polymer films, and semiconductor or adsorbent films in the case of carbon films. In embodiments where the precursor particles have an organic polymer composition, the organic polymer can be, for example, an addition polymer or copolymer (e.g., based on acrylate, methyl acrylate, methacrylate, methylmethacrylate, acrylamide, vinylidene fluoride), a conjugated or conducting polymer (e.g., polyphenylene vinylene), a ROMP polymer, a polyester, polyamide, or polyurethane.

In some embodiments, the non-pulsed or pulsed thermal method may, if desired, change the composition of the polymer, e.g., into a crosslinked, oxidized, or carbonized form. In other embodiments, the non-pulsed or pulsed thermal method is conducted such that a film of the polymer is produced while preserving the original composition of the polymer. In embodiments where the precursor particles have a carbon composition, the carbon composition can be any of the numerous compositions and allotropes of carbon particles known in the art. Some examples of carbon particles considered herein include carbon powder, carbon nanotubes, and the fullerenes. Other examples of carbon-containing particles are those having a metal carbide composition, such as silicon carbide, tungsten carbide, titanium carbide, and boron carbide. In some embodiments, any one or more of the foregoing classes or specific types of organic precursor particles may be excluded from the method.

In a second set of embodiments, the particles considered herein (and/or the resulting film), or a portion thereof, have an inorganic composition. For the purposes of this application, an inorganic composition is one not containing carbon. For example, in some embodiments, the inorganic precursor particles are composed of, or include, at least one metal, particularly one or a combination of transition metals. Some examples of such particles, particularly nanoparticles, include those composed of one or more late transition or noble metals, such as those selected from cobalt, nickel, copper, rhodium, palladium, silver, iridium, platinum, and gold, or an alloy or core-shell particle containing two, three, or more of these metals, or any of these metals in combination with one or other metals, particularly other transition metals, such as iron or manganese. Some examples of mixed-metal particle compositions include FePt, FePd, FeAu, FePtAu, FePdAu, FePdPt, CoPt, CoPd, CoAu, CoPtAu, CoPdAu, CoPdPt, NiPt, NiPd, NiAu, NiPtAu, NiPdAu, NiPdPt, FeCoPt, FeCoPd, FeCoAu, FeCoPtAu, FeCoPdAu, FeCoPdPt, FeNiPt, FeNiPd, FeNiAu, FeNiPtAu, FeNiPdAu, FeNiPdPt, NiCoPt, NiCoPd, NiCoAu, NiCoPtAu, NiCoPdAu, and NiCoPdPt compositions (or particular stoichiometries thereof, e.g., $Fe_{52}Pt_{48}$ and $Fe_{41}Ni_{12}Pt_{47}$), several of which are useful as magnetic media. Absence of a subscript does not necessarily indicate a stoichiometry of 1, but rather, any non-zero integral or fractional subscript that abides by the rules of chemistry, such as any of the exemplary values given for x hereinbelow. In some embodiments, any one or more of the foregoing classes or specific types of inorganic precursor particles may be excluded from the method.

In other embodiments, the inorganic precursor particles (and/or resulting film) have a metal-(main group metal) compound composition, where the term "metal" refers to either a single metal or a combination of metals. The main group metals considered herein include those of Groups III (boron group), IV (silicon group), V (nitrogen group), VI (oxygen group), and VII (halogen group). Some examples of metal-(main group metal) compound compositions include the borides, aluminides, silicides, germanides, nitrides, phosphides, arsenides, antimonides, oxides, sulfides, selenides, tellurides, fluorides, chlorides, bromides, and iodides of the alkali metals, alkaline earth metals, transition metals, lanthanides, and main group metals (i.e., mixed-main group metal compositions, such as boron nitride or indium phosphide). In some embodiments, at least a portion of the particles contains at least one transition metal (e.g., at least one late transition metal) and/or at least one main group metal (e.g., at least one main group metal selected from Group V and/or Group VI). In some embodiments, any one or more of the foregoing types of inorganic precursor particles may be excluded from the method.

In particular embodiments, the precursor particles (and/or resulting film) have a non-oxide semiconductor type of composition. The non-oxide semiconductor composition may, for example, contain one or more chalcophile elements in a positive oxidation state, and one or more main group metals selected from Groups V and VI of the Periodic Table of the Elements (hereinafter, the "Periodic Table"). Some examples of non-oxide semiconductor compositions include the sulfides, selenides, tellurides, nitrides, phosphides, arsenides, and antimonides of any of the metals describe above, particularly those of the late transition metals (e.g., Cu, Ni, Cd, Zn, and Ag) and early main group metals (e.g., B, Al, Ga, and In). The chalcophile metal is one, as known in the art, which has a propensity for forming metal-chalcogenide (i.e., metal-sulfide, metal-selenide, and metal-telluride) compositions. Some examples of chalcophile metals include, for example, V, Cr, Mn, Fe, Co, Ni, Cu, Zn, Mo, W, Pd, Pt, Au, Ag, Cd, Hg, Al, Ga, In, Tl, Ge, Sn, Pb, Sb, and Bi. Some metals particularly considered herein in the composition of the precursor particles include Cu, Al, Cd, Zn, Ga, Sn, and In. In some embodiments, any one or more of the foregoing classes or specific types of non-oxide particles may be excluded from the method.

In some embodiments, the precursor particles (and/or resulting film) have a quantum dot type of composition. Some examples of particle compositions having a quantum dot composition include CdS, CdSe, CdTe, $CdS_xSe_{1-x}$, $Cd_3As_2$, ZnS, ZnSe, ZnTe, $ZnS_xSe_{1-x}$, $Zn_3As_2$, $Ga_2S_3$, $Ga_2Se_3$, $Ga_2Te_3$, GaAs, GaAsP, $In_2S_3$, $In_2Se_3$, $In_2Te_3$, InAs, InAsP, $Cu_2S$, CuS, CuSe, CuTe, CuSeTe, $Cu_3P$, $Cu_3As$, $Cu_3As_2$, $Ag_3P$, $Ag_3As$, $Cu_3As_2$, $Cu_2AgP$, $CuAg_2P$, $CuGaSe_2$, $CuGaTe_2$, CuGaSSe, CuGaSeTe, CuGaSTe, $CuInS_2$, $CuInSe_2$, $CuInTe_2$, CuInSSe, CuInSeTe, CuInSTe, CuGaInS, CuGaInSe, CuGaInTe, CuGaInSSe, CuGaInSeTe, CuGaInSTe, FeSe, $Fe_3As_2$, FeAs, PbS, PbSe, PbTe, $Pb_3As_2$, HgS, HgSe, HgTe, $Cd_xZn_{1-x}Te$, $Cd_xHg_{1-x}Te$, $Hg_xZn_{1-x}Te$, $Cd_xZn_{1-x}S$, $Cd_xZn_{1-x}Se$, $Cd_xZn_{1-x}S_ySe_{1-y}$, $C_{1-x}Zn_{1-x}S_ySe_{1-y}$, $Ni_xZn_{1-x}S_ySe_{1-y}$, $Mn_xZn_{1-x}S_ySe_{1-y}$, $Cd_xHg_{1-x}Se$, $Hg_xZn_{1-x}Se$, $Pb_xSn_{1-x}Te$, $Ga_xIn_{2-x}Se_3$, $Ga_xIn_{1-x}As$, $AgGaS_2$, $AgGaSe_2$, $AgGaTe_2$, AgGaSSe, AgGaSeTe, AgGaSTe, $AgInS_2$, $AgInSe_2$, $AgInTe_2$, AgInSSe, AgInSeTe, AgInSTe, AgGaInS, AgGaInSe, AgGaInTe, AgGaInSSe, AgGaInSeTe, AgGaInSTe, $AuGaS_2$, $AuGaSe_2$, $AuGaTe_2$, $AuInS_2$, $AuInSe_2$, $AuInTe_2$, $TlGaS_2$, $TlGaSe_2$, $TlGaTe_2$, $TlInS_2$, $TlInSe_2$, $TlInTe_2$, and $Al_xGa_{1-x}As$ wherein x and y are, independently, an integral or non-integral numerical value greater than 0 and less than or equal to 1 (or less than or equal to 2 for the expression 2-x). An indicated subscript can be meant to be a precise value, as indicated, or can fractionally diverge from said value. Furthermore, absence of a subscript does not necessarily indicate a stoichiometry of 1, but rather, any non-zero integral or fractional subscript that abides by the rules of chemistry, such as any of the exemplary values given for x hereinbelow. In some embodiments, any one or more of the foregoing classes or specific types of quantum dot particles may be excluded from the method.

In other embodiments, the precursor particles (and/or resulting film) have a CIGs composition encompassed by the following general formula:

$$Cu(In_xGa_{1-x})X_2 \qquad (1)$$

In formula (1) above, X represents at least one non-metal selected from S, Se, and Te, and x is an integral or non-integral numerical value of or greater than 0 and less than or equal to 1, and. In different embodiments, X represents S, Se, Te, or a combination of two or three of these elements. X can also be represented by the formula $S_jSe_kTe_m$, wherein j, k, and m are independently 0 or an integral or non-integral numerical value greater than 0 and less than or equal to 1, provided that the sum of j, k, and m is 1. Compositions according to formula (1) and subformulas encompassed therein are collectively referred to herein as CIGs compositions. The CIGs compositions encompassed by formula (1) may also contain a relative molar ratio of Cu that diverges from 1 (e.g., precisely or about 0.5, 0.6, 0.7, 0.8, 0.85, 0.9, 0.95, or a range therein, or between any of said numbers and 1). In different embodiments, x has a value of precisely, about, up to, at least, or less than 0.01, 0.02, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.98, or 0.99, or a value within a range bounded by any two of the foregoing exemplary values. The particles may have a highly uniform and precise stoichiometric composition, particularly when produced by the microbial-mediated method, as further discussed below. Some examples of such precise stoichiometric compositions include $Cu(In_{0.74}Ga_{0.26})Se_2$ and $Cu_{0.87}(In_{0.74}Ga_{0.31})Se_2$. In some embodiments, any one or more classes or specific types of CIGs particles disclosed herein, including any of those described below, may be excluded from the method.

In particular embodiments, the CIGs composition is according to the following sub-formula:

$$CuIn_xGa_{1-x}S_2 \qquad (1a)$$

Some specific examples of compositions according to formula (1a) include $CuInS_2$, $CuIn_{0.9}Ga_{0.1}S_2$, $CuIn_{0.8}Ga_{0.2}S_2$, $CuIn_{0.7}Ga_{0.3}S_2$, $CuIn_{0.6}Ga_{0.4}S_2$, $CuIn_{0.5}Ga_{0.5}S_2$, $CuIn_{0.4}Ga_{0.6}S_2$, $CuIn_{0.3}Ga_{0.7}S_2$, $CuIn_{0.2}Ga_{0.8}S_2$, $CuIn_{0.1}Ga_{0.9}S_2$, and $CuGaS_2$.

In other particular embodiments, the CIGs composition is according to the following sub-formula:

$$CuIn_xGa_{1-x}Se_2 \qquad (1b)$$

Some specific examples of compositions according to formula (1b) include $CuInSe_2$, $CuIn_{0.9}Ga_{0.1}Se_2$, $CuIn_{0.8}Ga_{0.2}Se_2$, $CuIn_{0.7}Ga_{0.3}Se_2$, $CuIn_{0.6}Ga_{0.4}Se_2$, $CuIn_{0.5}Ga_{0.5}Se_2$, $CuIn_{0.4}Ga_{0.6}Se_2$, $CuIn_{0.3}Ga_{0.7}Se_2$, $CuIn_{0.2}Ga_{0.8}Se_2$, $CuIn_{0.1}Ga_{0.9}Se_2$, and $CuGaSe_2$.

In yet other particular embodiments, the CIGs composition is according to the following sub-formula:

$$CuIn_xGa_{1-x}Te_2 \qquad (1c)$$

Some specific examples of compositions according to formula (1c) include $CuInTe_2$, $CuIn_{0.9}Ga_{0.1}Te_2$, $CuIn_{0.8}Ga_{0.2}Te_2$, $CuIn_{0.7}Ga_{0.3}Te_2$, $CuIn_{0.6}Ga_{0.4}Te_2$, CuIn$_{0.5}$Ga$_{0.5}$Te$_2$, CuIn$_{0.4}$Ga$_{0.6}$Te$_2$, CuIn$_{0.3}$Ga$_{0.7}$Te$_2$, CuIn$_{0.2}$Ga$_{0.8}$Te$_2$, CuIn$_{0.1}$Ga$_{0.9}$Te$_2$, and CuGaTe$_2$.

In other embodiments, the precursor particles (and/or resulting film) have a kesterite-type composition encompassed by the following general formula:

$$M_3SnX_4 \qquad (2)$$

In formula (2), M represents at least one chalcophile (typically divalent) metal other than Sn, and X is as defined above under formula (1). In particular embodiments, M represents one, two, three, or four metals selected from Cu, Fe, Zn, and Cd. In different embodiments, X represents S, Se, Te, or a combination of two or three of these elements. The relative molar ratio of Sn encompassed by formula (2) may diverge from 1, and the relative molar ratio of M may diverge from 3. In some embodiments, any one or more classes or specific types of kesterite-type particles disclosed herein, including any of those described below, may be excluded from the method.

In some embodiments, the kesterite-type compositions of formula (2) are encompassed by the following sub-generic formula:

$$Cu_{3-x}M'_xSnX_4 \qquad (2a)$$

In formula (2a), M' represents one or more chalcophile metals other than Cu, and X is as defined above. In particular embodiments, M' represents one, two, or three metals selected from any chalcophile metal, such as, for example, V, Cr, Mn, Co, Ni, Fe, Zn, Cd, Cu, Mo, W, Pd, Pt, Au, Ag, Hg, Al, Ga, In, Tl, Ge, Sn, Pb, Sb, and Bi. Some metals particularly considered herein include Fe, Zn, and Cd. The subscript x is an integral or non-integral numerical value of or greater than 0 and up to or less than 1, 2, or 3. In different embodiments, x can be selected to be a value of precisely, about, up to, or less than, for example, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3, or a value within a range bounded by any two of the foregoing exemplary values.

Some particular kesterite-type compositions of formula (2a) are encompassed by the following sub-generic formula:

$$Cu_{3-x}Zn_xSnX_4 \qquad (2a-1)$$

In formula (2a-1), x and X are as described above under formula (2a). Some specific examples of compositions according to formula (2a-1) when X is S include Cu$_3$SnS$_4$ (kuramite), Cu$_2$ZnSnS$_4$ (kesterite), CuZn$_2$SnS$_4$, Cu$_{0.5}$Zn$_{2.5}$SnS$_4$, Cu$_{2.5}$Zn$_{0.5}$SnS$_4$, Cu$_{1.5}$Zn$_{1.5}$SnS$_4$, and Zn$_3$SnS$_4$. Other examples of compositions according to formula (2a-1) are provided by replacing S in the foregoing examples with Se or Te, or X may be a combination of elements selected from S, Se, and Te. The relative molar ratio of Sn encompassed by formula (2a-1) may diverge from 1.

Other particular kesterite-type compositions of formula (2a) are encompassed by the following sub-generic formula:

$$Cu_{3-x}Fe_xSnX_4 \qquad (2a-2)$$

In formula (2a-2), X and x are as described above under formula (2a). Some specific examples of compositions according to formula (2a-2) when X is S include Cu$_3$SnS$_4$, Cu$_2$FeSnS$_4$ (stannite), CuFe$_2$SnS$_4$, Cu$_{0.5}$Fe$_{2.5}$SnS$_4$, Cu$_{2.5}$Fe$_{0.5}$SnS$_4$, Cu$_{1.5}$Fe$_{1.5}$SnS$_4$, and Fe$_3$SnS$_4$. Other examples of compositions according to formula (2a-2) are provided by replacing S in the foregoing examples with Se or Te, or X may be a combination of elements selected from S, Se, and Te. The relative molar ratio of Sn encompassed by formula (2a-2) may diverge from 1.

Other particular kesterite-type compositions of formula (2a) are encompassed by the following sub-generic formula:

$$Cu_{3-x}Cd_xSnX_4 \qquad (2a-3)$$

In formula (2a-3), x and X are as described above under formula (2a). Some specific examples of compositions according to formula (2a-3) when X is S include Cu$_3$SnS$_4$, Cu$_2$CdSnS$_4$ (cernyite), CuCd$_2$SnS$_4$, Cu$_{0.5}$Cd$_{2.5}$SnS$_4$, Cu$_{2.5}$Cd$_{0.5}$SnS$_4$, Cu$_{1.5}$Cd$_{1.5}$SnS$_4$, and Cd$_3$SnS$_4$. Other examples of compositions according to formula (2a-3) are provided by replacing S in the foregoing examples with Se or Te, or X may be a combination of elements selected from S, Se, and Te. The relative molar ratio of Sn encompassed by formula (2a-3) may diverge from 1.

In other embodiments, the kesterite-type compositions of formula (2) are encompassed by the following sub-generic formula:

$$Cu_2M'_xM'_{1-x}SnX_4 \qquad (2b)$$

In formula (2b), each M' is defined as above under formula (2a), X is as defined above, and x is an integral or non-integral numerical value of or greater than 0 and up to or less than 1. In particular embodiments, the two M' metals in formula (2b) are not the same, i.e., the two M' metals in formula (2b) are different. The relative molar ratio of Sn encompassed by formula (2b) may diverge from 1, and the relative molar ratio of Cu encompassed by formula (2b) may diverge from 2.

Some particular kesterite-type compositions of formula (2b) are encompassed by the following sub-generic formula:

$$Cu_2Fe_xZn_{1-x}SnX_4 \qquad (2b-1)$$

Some specific examples of compositions according to formula (2b-1) when X is S include Cu$_2$Fe$_{0.1}$Zn$_{0.9}$SnS$_4$, Cu$_2$Fe$_{0.2}$Zn$_{0.8}$SnS$_4$, Cu$_2$Fe$_{0.3}$Zn$_{0.7}$SnS$_4$, Cu$_2$Fe$_{0.4}$Zn$_{0.6}$SnS$_4$, Cu$_2$Fe$_{0.5}$Zn$_{0.5}$SnS$_4$, Cu$_2$Fe$_{0.6}$Zn$_{0.4}$SnS$_4$, Cu$_2$Fe$_{0.7}$Zn$_{0.3}$SnS$_4$, Cu$_2$Fe$_{0.8}$Zn$_{0.2}$SnS$_4$, and Cu$_2$Fe$_{0.9}$Zn$_{0.1}$SnS$_4$. Other examples of compositions according to formula (2b-1) are provided by replacing S in the foregoing examples with Se or Te, or X may be a combination of elements selected from S, Se, and Te. The relative molar ratio of Sn encompassed by formula (2b-1) may diverge from 1, and the relative molar ratio of Cu encompassed by formula (2b-1) may diverge from 2.

In other embodiments, the kesterite-type compositions of formula (2) are encompassed by the following sub-generic formula:

$$CuM'_xM'_{2-x}SnX_4 \qquad (2c)$$

In formula (2c), each M' is defined as above under formula (2a), X is as defined above, and x is an integral or non-integral numerical value of at least or greater than 0 and up to or less than 1 or 2. In particular embodiments, the two M' metals in formula (2c) are not the same, i.e., the two M' metals in formula (2c) are different. In different embodiments, x can be selected to be a value of precisely or about 1 or 2, or a non-integral value between 0 and 2, wherein the term "about" is as defined under formula (2a). The relative molar ratio of Sn and Cu encompassed by formula (2c) may each diverge from 1.

Some particular kesterite-type compositions of formula (2c) are encompassed by the following sub-generic formula:

$$CuFe_xZn_{2-x}SnS_4 \qquad (2c-1)$$

Some specific examples of compositions according to formula (2c-1) when X is S include CuFe$_{0.5}$Zn$_{1.5}$SnS$_4$, CuFeZnSnS$_4$, and CuFe$_{1.5}$Zn$_{0.5}$SnS$_4$. Other examples of compositions according to formula (2c-1) are provided by replacing S in the foregoing examples with Se or Te, or X may be a combination of elements selected from S, Se, and Te. The relative molar ratio of Sn and Cu encompassed by formula (2c-1) may each diverge from 1.

In other embodiments, the precursor particles (and/or resulting film) have a composition suitable as a lithium battery electrode. Some examples of such compositions particularly suitable as battery cathodes include $LiFePO_4$, $Li_2FePO_4F$, and the class of compounds represented by the formula $LiMO_2$, wherein M is one or a combination of alkaline earth and/or transition metals, particularly those metals selected from Mn, Fe, Co, Ni, and Mg. A particular subclass of battery cathode materials considered herein are those within the formula $Li(Ni_xMn_yCo_z)O_2$, wherein x, y, and z are each selected from an integer of 0 to 1, provided that x, y, and z add to 1. Some compositions suitable as a battery anode material include lithium carbide (e.g., $LiC_6$) and $Li_4Ti_5O_{12}$. In some embodiments, any one or more of the foregoing classes or specific types of lithium battery electrode particles may be excluded from the method.

In other embodiments, the precursor particles (and/or resulting film) have a composition suitable as a thermoelectric material. Some examples of such compositions include bismuth telluride ($Bi_2Te_3$), bismuth selenide ($Bi_2Se_3$), lead telluride (PbTe), lead selenide (PbSe), the skutterudites (generally, cobalt arsenide with varying amounts of nickel and iron), and $Ca_4Co_3O_9$. In some embodiments, any one or more of the foregoing classes or specific types of thermoelectric particles may be excluded from the method.

In yet other embodiments, the precursor particles (and/or resulting film) have a superconducting composition. The superconducting composition can, for example, include a rare-earth (RE) or transition metal (TM) barium copper oxide composition (hereinafter, a "metal-barium-copper-oxide" composition). The rare earth element can be any of the lanthanide or actinide metals listed in the Periodic Table and as exemplified above. The lanthanide metals refer predominantly to the elements of the Periodic Table having an atomic number of 57 to 71. The actinide metals generally refer to any of the elements of the Periodic Table having an atomic number of 90 to 103. The transition metals generally refer to any of the elements located in Groups 3-12 of the Periodic Table (i.e., the corresponding scandium through zinc groups). In some embodiments, any one or more classes or specific types of superconducting particles disclosed herein, including any of those described below, may be excluded from the method.

In a particular embodiment, the metal-barium-copper-oxide material is according to the formula $(RE)Ba_2Cu_3O_7$, wherein RE is a rare earth or transition metal element. Some examples of suitable RE metals include yttrium (Y), lanthanum (La), cerium (Ce), neodymium (Nd), samarium (Sm), europium (Eu), gadolinium (Gd), terbium (Tb), thulium (Tm), ytterbium (Yb), lutetium (Lu), and combinations thereof. In further embodiments, the superconducting composition is a yttrium-barium-copper-oxide (YBCO) material, e.g., as generally described by the formula $YBa_2Cu_3O_{7-x}$, wherein x is generally a number within the approximate range $0 \leq x \leq 1$. Some examples of other types of yttrium barium copper oxide compositions include $Y_3Ba_4Cu_7O_{16}$, $Y_2Ba_4Cu_7O_{15}$, $Y_2CaBa_4Cu_7O_{16}$, $(Y_{0.5}Lu_{0.5})Ba_2Cu_3O_7$, $(Y_{0.5}Tm_{0.5})Ba_2Cu_3O_7$, and $(Y_{0.5}Gd_{0.5})Ba_2Cu_3O_7$.

The superconducting composition can also be a thallium-containing barium copper oxide composition, such as a thallium-barium-calcium-copper-oxide composition (e.g., of the formula $TlBa_2Ca_{n-1}Cu_nO_{2n+3}$, wherein n is generally a number greater than 1 and up to 4). The superconducting composition can also be a mercury-containing barium copper oxide material, such as a mercury-barium-calcium-copper-oxide composition (e.g., of the formula $HgBa_2Ca_{n-1}Cu_nO_{2n+2}$, wherein n is a number greater than 1 and up to 4). The superconducting composition can also be a bismuth- and/or strontium-containing calcium-copper-oxide composition, such as a bismuth-strontium-calcium-copper-oxide (BSCCO) composition (e.g., of the formula $Bi_2Sr_2Ca_nCu_{n+1}O_{2n+6}$). The superconducting composition can also be a lanthanum-containing copper oxide composition (e.g., of the formula $La_{2-x}M_xCuO_4$, wherein x is greater than zero and less than 2, and M is an alkaline earth metal ion, such as Mg, Ca, Sr, or Ba). Some specific examples of such superconducting compositions include $La_{1.85}Ba_{0.15}CuO_4$ (LBCO) and $La_{1.85}Sr_{0.15}CuO_4$ (LSCO).

In other embodiments, the precursor particles (and/or resulting film) have a mixed-element oxide composition. Numerous of the superconducting compositions, as exemplified above, are in this class. Mixed-element oxide thin films are used in numerous technologies, including as matrix materials, light-emitting materials (e.g., light-emitting diodes and lasers), cathode ray tubes, magnetic materials, electrode materials, and semiconducting materials. Some examples of other such compositions include indium tin oxide (ITO); yttrium aluminum garnet (e.g., $Y_3Al_5O_{12}$); yttrium iron garnet (e.g., $Y_3Fe_2(FeO_4)_3$); yttrium oxide-sulfide; the magnesium aluminum oxides, and more particularly, the barium magnesium aluminum oxides (e.g., $BaMg_2Al_{16}O_{27}$); transition metal silicates (e.g., $Zn_2SiO_4$, $Y_2SiO_5$, and $CaSiO_3$); the metal phosphates and vanadates, and more particularly, the rare earth metal phosphates and vanadates (e.g., $LaPO_4$ and $YVO_4$); and the metal aluminum oxides ($SrAl_2O_7$). In some embodiments, any one or more classes or specific types of mixed-element oxide particles disclosed herein, including any of those described below, may be excluded from the method.

In particular embodiments, the mixed-element oxide composition is a perovskite-type oxide according to the chemical formula.

$$M'M''O_3 \tag{3}$$

In formula (3), M' and M" are independently monovalent, divalent, trivalent, tetravalent, or pentavalent metal ions, provided that the sum of oxidation states of M' and M" add to +6 to charge balance with oxide atoms. For example, M' can be a monovalent metal ion and M" a pentavalent metal ion, or M' can be a divalent metal ion and M" a tetravalent metal ion, or M' and M" can both be trivalent metal ions.

Some examples of perovskite-type compositions wherein M' is a monovalent metal ion and M" is a pentavalent metal ion include $LiNbO_3$, $LiTaO_3$, $NaNbO_3$, $CuTaO_3$, and $AgNbO_3$. Some examples of perovskite-type compositions wherein M' is a divalent metal ion and M" is a tetravalent metal ion include the ferrites (e.g., $BaFeO_3$, $SrFeO_3$, and $CaFeO_3$), the zirconates (e.g., $MgZrO_3$, $CaZrO_3$, $SrZrO_3$, $BaZrO_3$, and $CdZrO_3$), the titanates (i.e., of the general formula $M'TiO_3$ wherein M' is a divalent metal ion, e.g., $MgTiO_3$, $CaTiO_3$, $SrTiO_3$, $BaTiO_3$, $FeTiO_3$, and $PbTiO_3$), the cerates (e.g., $MgCeO_3$, $CaCeO_3$, and $SrCeO_3$), the tungstates (e.g., $MgWO_3$, $CaWO_3$), the manganates (e.g., $MgMnO_3$, $CaMnO_3$, $SrMnO_3$, $BaMnO_3$, $ZnMnO_3$, and $CdMnO_3$), and the metasilicates (e.g., $MgSiO_3$, $CaSiO_3$, $SrSiO_3$, and $BaSiO_3$). Some examples of perovskite-type materials wherein M' and M" are both trivalent metal ions include materials of the general formulas $(RE)M''O_3$, wherein RE represents any one or combination of the rare earth metals (in trivalent form) described above. In particular embodiments, M' and M" independently represent any one or combination of metal ions selected from trivalent transition metal, main group, and rare earth metal ions. The formula $(RE)M''O_3$ can encompass, for example, any of the subclasses YM"O₃, LaM"O₃, CeM"O₃, PrM"O₃, NdM"O₃, PmM"O₃, SmM"O₃, EuM"O₃, GdM"O₃, TbM"O₃, DyM"O₃, HoM"O₃, ErM"O₃, TmM"O₃, YbM"O₃, and LuM"O₃, wherein M" represents one or a combination of trivalent metal ions, or in particular embodiments, one or a combination of metals selected from trivalent transition metals, trivalent rare earth metals, and/or trivalent main group metals. The corresponding perovskite-type sulfides, selenides, and tellurides are also considered herein.

In other particular embodiments, the mixed-element oxide composition is a spinel-type oxide according to the chemical formula:

$$M'M''_2O_4 \quad (4)$$

In formula (4), M' and M" are independently monovalent, divalent, trivalent, tetravalent, pentavalent, or hexavalent metal ions, provided that the sum of oxidation states of M' and M" add to +8 to charge balance with oxide atoms. For example, M' can be a divalent metal ion and M" a trivalent metal ion, or M' can be a tetravalent metal ion and M" a divalent metal ion.

Some examples of spinel-type compositions according to formula (4) wherein M' is a divalent metal ion and M" is a trivalent metal ion include materials of the general formula $M'V_2O_4$ wherein M' is a divalent metal (e.g., $MnV_2O_4$ and $NiV_2O_4$), materials of the general formula $M'Cr_2O_4$ wherein M' is a divalent metal (e.g., $MnCr_2O_4$, $CuCr_2O_4$), materials of the general formula $M'Mn_2O_4$ wherein M' is a divalent metal (e.g., $FeMn_2O_4$, $CoMn_2O_4$, $NiMn_2O_4$, and $CuMn_2O_4$), materials of the general formula $M'Fe_2O_4$ wherein M' is a divalent metal (e.g., $Fe^{2+}Fe^{3+}_2O_4$, $MnFe_2O_4$, $CoFe_2O_4$, $NiFe_2O_4$, and $CuFe_2O_4$), materials of the general formula $M'Co_2O_4$ wherein M' is a divalent metal, materials of the general formula $M'Ni_2O_4$ wherein M' is a divalent metal (e.g., $MnNi_2O_4$), materials of the general formula $M'Al_2O_4$ wherein M' is a divalent metal (e.g., $MnAl_2O_4$, $NiAl_2O_4$, and $CuAl_2O_4$), materials of the general formula $M'Ga_2O_4$ wherein M' is a divalent metal (e.g., $MnGa_2O_4$, $NiGa_2O_4$, $ZnGa_2O_4$, and $CuGa_2O_4$), materials of the general formula $M'In_2O_4$ wherein M' is a divalent metal (e.g., $CuIn_2O_4$, $MgIn_2O_4$, and $CaIn_2O_4$), and materials of the general formula $M'(RE)_2O_4$ wherein M' is a divalent metal and RE is a rare earth lanthanide or actinide trivalent metal, (e.g., $MnLa_2O_4$, $NiLa_2O_4$, and $CuLa_2O_4$). M' and/or M" can also represent a combination of metals, such as in $(BaCu)_2Cr_2O_4$, $(Fe,Mg)Cr_2O_4$, $(Ca,Mg)Cr_2O_4$, $Ca(V,Cr)_2O_4$, $Ba(Fe, Co)_2O_4$, and $(Ca,Sr)(Mn,Fe)_2O_4$. Some examples of spinel-type materials according to formula (4) wherein M' is a tetravalent metal ion and M" is a divalent metal ion include those of the formula $ZrM''_2O_4$, such as $ZrMg_2O_4$, $ZrNi_2O_4$, and $ZrCu_2O_4$. The corresponding spinel-type sulfides, selenides, and tellurides are also considered herein.

Other spinel-type oxide compositions for the precursor particles and/or resulting film include those having the composition $M_xFe_{3-x}O_4$, wherein M is one or a combination of metals selected from transition, rare earth, and main group metals (e.g., Al, Ga, or In), particularly where M is a trivalent element. In particular embodiments, M is one or a combination of metals selected from Cr, Mn, Co, Ni, Cu, Zn, Gd, Nd, Tb, Ho, and Er. Such compositions are particularly considered herein as magnetic oxide compositions. In the foregoing formula, the subscripted stoichiometry of Fe may diverge from 3 (e.g., as 2.5-x).

Other spinel-type oxide compositions for the precursor particles and/or resulting film include those having the composition $M_xZn_yGa_{3-x-y}O_4$, wherein M is one or a combination of metals selected from transition, rare earth, and main group metals. In particular embodiments, M is one or a combination of metals selected from Cr, Mn, Co, Eu, and Dy. Such compositions are particularly considered herein as phosphor compositions. In the foregoing formula, the subscripted stoichiometry of Ga may diverge from 3.

Any of the precursor particle and film compositions described above can include dopant amounts of a chemical species, either to render them as p- or n-type materials (e.g., phosphorus- and boron-doping), or to impart, adjust, or modulate a particular property, such as luminescence or phosphorescence. The dopant can be any metal or non-metal species, such as any of the metal and non-metal species described above. Rare earth dopants are often used to impart luminescence, phosphorescence, and other light-emitting (e.g., lasing) properties. Some examples of rare earth dopants include yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu), and combinations thereof. The dopants may also be selected from the transition metals (e.g., Ag, Zn, Cu, Ti, and Mn) and the main group metals (e.g., B, Al, Ga, In, N, P, As, and Sb). Generally, the dopant is present in an amount of less than 0.5 molar percent of the resulting composition, or in different embodiments, less than or up to 0.4, 0.3, 0.2, 0.1, 0.05, 0.02, or 0.01 molar percent of the resulting composition. Some examples of doped compositions include ZnS:Ni, wherein Ni functions as a dopant, as described in, for example, Bang et al., *Advanced Materials*, 20:2599-2603 (2008); $Zn_xCd_{1-x}S$ doped compositions, as described in Wang et al., *Journal of Physical Chemistry C* 112:16754-16758 (2008); and ZnS:Mn and ZnS:Cu compositions, as described in Song et al., *Journal of Physics and Chemistry of Solids*, 69:153-160 (2008). In other embodiments, a dopant is excluded, or alternatively, one or more of any of the generic or specific dopants described above are excluded.

A film can be produced by any of the methods described above, by either using a single type of precursor particles all possessing the composition desired for the resulting film, or by using more than one type of precursor particle that together, when processed, result in a film of the desired composition. For example, in embodiments where a CIGs film is to be prepared, the precursor particles can be any of the particles described above having a CIGs composition, or the precursor particles can be of different compositions, that, when combined and processed under the conditions used for forming the film, produce the desired CIGs film composition. In a first set of embodiments, a CIGs layer is produced by using a mixture of particles having two or three different binary compositions selected from compositions A, B, and C, wherein A is selected from CuS, $Cu_2S$, CuSe, $Cu_2Se$, $CuSe_2$, $Cu_9S_5$, $Cu_7S_4$, $Cu_9S_8$, $Cu_{1.4}S$, $Cu_3Se_2$, and $Cu_5Se_4$; B is selected from InS, $In_2S_3$, InSe, and $In_2Se_3$; and C is selected from GaS, $Ga_2S_3$, GaSe, and $Ga_2Se_3$. In a second set of embodiments, a CIGs layer is produced by using a mixture of particles having two different ternary compositions selected from compositions D and E, wherein D is selected from $CuInS_2$, $CuInSe_2$, $Cu_2InS_4$, and $Cu_2InSe_4$, and E is selected from $CuGaS_2$, $CuGaSe_2$, $Cu_2GaS_4$, and $Cu_2GaSe_4$. In a third set of embodiments, a CIGs layer is produced by using a mixture of particles having binary and ternary compositions selected from compositions A and F, where A is as provided above, and F is $InGaS_3$ or $InGaSe_3$.

In particular embodiments, the precursor particles considered herein possess at least one photoluminescence absorption or emission peak. The peak can be, for example, in the UV, visible, and/or IR range. In different embodiments, the photoluminescence peak is preferably located at, or at least, or above, or less than 200 nm, 250 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm, 1000 nm, 1020 nm, 1040 nm, 1060 nm, 1080 nm, 1100 nm, 1120 nm, 1140 nm, 1160 nm, 1180 nm, 1200 nm, 1220 nm, 1240 nm, 1260 nm, 1280 nm, 1300 nm, 1320 nm, 1340 nm, 1360 nm, 1380 nm, 1400 nm, 1420 nm, 1440 nm, 1460 nm, 1480 nm, 1500 nm, 1600 nm, 1700 nm, 1800 nm, 1900 nm, 2000 nm, 2500 nm, 3000 nm, 3500 nm, 4000 nm, 4500 nm, or 5000 nm, or within ±5 nm, 10 nm, 20 nm, 30 nm, 40 nm, 50 nm, 60 nm, 70 nm, 80 nm, 90 nm, or 100 nm of any of these values, or within a range bounded by any two of these values (e.g., 400-500 nm or 960-980 nm). Some particular ranges considered herein for photoluminescence peaks include 300-500 nm, 300-1500 nm, 500-1000 nm, 500-1500 nm, 435-445 nm, 430-450 nm, 475-525 nm, 1050-1150 nm, 970-980 nm, and 970-1000 nm. In particular embodiments, the nanoparticles described herein exhibit a photoluminescence peak above 500 nm, 800 nm, 1000 nm, 1200 nm, or 1500 nm.

In some embodiments, the particles (and/or resulting film) possess a photoluminescence peak characterized by a full-width half maximum (FWHM) value of about or less than 20 nanometers (20 nm). In other embodiments, the particles (and/or resulting film) possess a photoluminescence peak characterized by a FWHM value of about or greater than 20 nm. In different embodiments, the particles (and/or resulting film) possess a photoluminescence peak characterized by a FWHM value of about or at least, or above, or less than 20 nm, 40 nm, 60 nm, 80 nm, 100 nm, 150 nm, 200 nm, 250 nm, 300 nm, 350 nm, 400 nm, 450 nm, 500 nm, 600 nm, 700 nm, 800 nm, 900 nm, 1,000 nm, 1,100 nm, and 1,200 nm. In yet other embodiments, the particles (and/or resulting film) possess a photoluminescence peak having a FWHM value of about or less than 15 nm, 10 nm, 8 nm, or 5 nm.

For producing the precursor particles, particulate forms of any of the above-described compositions can be prepared by methods known in the art. In some embodiments, a chemical process is used. For example, particularly in the case of noble metal particles, reductants (e.g., the borohydrides, hydrazine, citric acid, or hypophosphite) are commonly used to reduce metal ions in solution to particles containing low valent or zerovalent forms of the metal ions. The chemical method may additionally include, for example, arrested precipitation in solution, co-precipitation (particularly useful in producing iron oxide nanoparticles), a microemulsion technique, sol-gel method, chemical vapor deposition (CVD), or a physical decomposition technique in solution (e.g., ultrasonication), all of which are well-known in the art. In other embodiments, a physical process is used. Some examples of physical processes include high temperature pyrolysis, solvothermal methods, sonochemical methods, and physical vapor deposition.

In particular embodiments, quantum dot particles are produced by arrested precipitation. For example, cadmium selenide can be synthesized by arrested precipitation in solution by reacting dialkylcadmium (i.e., $R_2Cd$) and trioctylphosphine selenide (TOPSe) precursors in a solvent at elevated temperatures, i.e.,

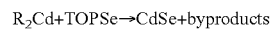

$R_2Cd + TOPSe \rightarrow CdSe + byproducts$

Multi-element particles described above, particularly CIGs and kesterite-type particles, can be produced by any of the methods known in the art. Some of these methods include physical deposition methods, such as advanced epitaxial, ion implantation, lithographic techniques, and high temperature pyrolysis. For example, CdSe nanoparticles can be produced using high temperature pyrolysis by preparing an aerosol containing a mixture of volatile cadmium and selenium precursors, and then subjecting the aerosol to high temperatures (e.g., by carrying through a furnace) in the presence of an inert gas. Under these conditions, the precursors react to form the semiconductor nanoparticles (e.g., CdSe) and byproducts.

In particular embodiments considered herein, the multi-element particles are produced by microbial-mediated particle synthesis. A detailed description of the microbial-mediated process is provided in, for example, U.S. Application Publication Nos. 2010/0193752, 2010/0184179, 2010/0193752, and 2010/0330367, the contents of which are herein incorporated by reference in their entirety.

There are several advantages provided by the microbial-mediated process, particularly as described in U.S. Application Publication No. 2010/0193752. The microbial-mediated process is, for example, generally more capable of producing particles in significant quantities in a more cost-effective manner than processes of the art. Another significant advantage of the microbial-mediated process is its ability to exercise a significantly increased level of precision and control of the physical (e.g., size, shape, and crystalline form), compositional (particularly in achieving precise stoichiometries), electronic or photonic characteristics, and degree of physical and compositional uniformity of the resulting particles.

In the microbial-mediated method, a first precursor metal component (for example, one that is a chalcophile, i.e., can form semiconducting chalcogenide compounds) and a second precursor metal component (e.g., one containing a chalcogen element) are processed by anaerobic microbes in a manner that produces particles having a mixed-metal composition, such as a non-oxide semiconductor composition. In particular embodiments, the first precursor metal component includes one or more transition metals, and the second precursor metal component includes one or more main group metals (e.g., one or more chalcogens). As the precursor metal components are combined to make the particles, generally, the resulting particles have a composition containing each of the precursor metals. Such variables as the composition, concentration, and processing temperature of the precursor metal components can be adjusted to produce particles having a desired composition or physical characteristic, such as a particular stoichiometric composition, a particular phase (e.g., single-crystalline, polycrystalline, or amorphous), a particular size, a degree of uniformity in size (e.g., polydispersed vs. substantially monodisperse), and/or a particular shape.

In particular embodiments of the microbial-mediated method, the first precursor metal component includes one or more types of metals in ionic form. The one or more metals are typically in the form of a salt or coordination compound, or a colloidal hydrous metal oxide or mixed metal oxide, wherein "compound" as used herein also includes a "material" or "polymer". Some examples of first precursor metal compounds applicable herein include the metal halides (e.g., $CuCl_2$, $CdCl_2$, $ZnCl_2$, $ZnBr_2$, $GaCl_3$, $InCl_3$, $FeCl_2$, $FeCl_3$, $SnCl_2$, and $SnCl_4$), metal nitrates (e.g., $Cd(NO_3)_2$, $Ga(NO_3)_3$, $In(NO_3)_3$, and $Fe(NO_3)_3$), metal perchlorates, metal carbonates (e.g., $CdCO_3$), metal sulfates (e.g., $CdSO_4$, $FeSO_4$, and $ZnSO_4$), metal oxides (e.g., $Fe_2O_3$, $CdO$, $Ga_2O_3$, $In_2O_3$, $ZnO$, $SnO$, $SnO_2$), metal hydroxides (e.g., $Fe(OH)_3$ and $Zn(OH)_2$), metal oxyhydroxides (e.g., FeOOH, or FeO(OH), and their alternate forms), metal-EDTA complexes, metal amines (e.g., metal alkylamine, piperidine, pyridine, or bipyridine salt complexes), metal carboxylates (e.g., cadmium acetate), and metal acetylacetonate (i.e., metal-acac) complexes. One or more dopant species can be included in the precursor metal component in order to likewise dope the resulting particles.

When two or more metals are used as the first metal precursor component, the molar ratio of metal ions can be adjusted such that a particular molar ratio of metals is provided in the resulting particles. Typically, the molar ratio of metal ions in the metal component is the molar ratio of metals found in the resulting particles. However, the molar ratio of metals in the particles may, in several embodiments, differ from the molar ratio of metals in the metal component. In a particular embodiment, a desired molar ratio of metals is achieved in the particles by suitable adjustment of metal ratios in the precursor metal component.

In the microbial-mediated method, the total metal concentration should be below a concentration at which the metals are toxic to the microbes being used. Typically, the total metal concentration is no more than 100 mM. In different embodiments, the total metal concentration may preferably be no more than 90 mM, 80 mM, 70 mM, 60 mM, 50 mM, 40 mM, 30 mM, 20 mM, 15 mM, 10 mM, 5 mM, 1 mM, 0.5 mM, or 0.1 mM, or within a range resulting from any two of the above exemplary values.

In particular embodiments of the microbial-mediated method, the second precursor metal component includes one or more main group elements, such as one or more elements selected from O, S, Se, Te, N, P, As, Sb, B, Si, Ge, Al, Ga, and In (or in more particular embodiments, one or more element selected from O, S, Se, Te, N, P, As, and Sb). The main group component can include any suitable form of the main group elements, including, for example, the elemental or compound forms of these elements.

In some embodiments of the microbial-mediated method, the at least first and second precursor metal components include only main group metals. The foregoing embodiment is particularly desirable in producing particles having a mixed-(main group element) composition, such as BN, AlN, GaN, InN, AlGaN, AlInN, BAN, BAlGaN, AlGaInN, GaInN, BP, AlP, GaP, InP, AlGaP, AlInP, BAlP, BAlGaP, BGaInP, AlGaInP, GaInP, BAs, AlAs, GaAs, InAs, AlGaAs, AlInAs, BAlAs, BAlGaAs, AlGaInAs, GaInAs, as well as any of the III-VI compositions described above (e.g., the sulfides, selenides, and tellurides of aluminum, gallium, and indium). It is understood that the foregoing compositional formulas (e.g., AlGaP) are not meant to indicate any particular stoichiometric composition, but merely an indication of the different elements included in the composition. Each representation, particularly those containing three or more elements, may include numerous particular stoichiometries (e.g., $Ga_{0.5}In_{0.5}As$, $Ga_{0.2}In_{0.8}As$, and $Ga_{0.7}In_{0.3}As$).

In a first embodiment, the microbial-mediated process includes a source of sulfur. The source of sulfur can be, for example, elemental sulfur) ($S^0$) or a sulfur-containing compound. In one instance, the sulfur-containing compound is an inorganic sulfur-containing compound. Some examples of inorganic sulfur-containing compounds include the inorganic sulfates (e.g., $Na_2SO_4$, $K_2SO_4$, $MgSO_4$, $(NH_4)_2SO_4$, $H_2SO_4$, or a metal sulfate), the inorganic sulfites (e.g., $Na_2SO_3$, $H_2SO_3$, or $(NH_4)_2SO_3$), inorganic thiosulfates (e.g., $Na_2S_2O_3$ or $(NH_4)_2S_2O_3$), sulfur dioxide, peroxomonosulfate (e.g., $Na_2SO_5$ or $KHSO_5$), and peroxodisulfate (e.g., $Na_2S_2O_8$, $K_2S_2O_8$, or $(NH_4)_2S_2O_8$). In another instance, the sulfur-containing compound is an organosulfur (i.e., organothiol or organomercaptan) compound. The organosulfur compound contains at least one hydrocarbon group and is typically characterized by the presence of at least one sulfur-carbon bond. Some examples of suitable organosulfur compounds include the hydrocarbon mercaptans (e.g., methanethiol, ethanethiol, propanethiol, butanethiol, thiophenol, ethanedithiol, 1,3-propanedithiol, 1,4-butanedithiol, thiophene), the alcohol-containing mercaptans (e.g., 2-mercaptoethanol, 3-mercaptopropanol, 4-mercaptophenol, and dithiothreitol), the mercapto-amino acids (e.g., cysteine, homocysteine, methionine, thioserine, thiothreonine, and thiotyrosine), mercapto-peptides (e.g., glutathione), the mercapto-pyrimidines (e.g., 2-thiouracil, 6-methyl-2-thiouracil, 4-thiouracil, 2,4-dithiouracil, 2-thiocytosine, 5-methyl-2-thiocytosine, 5-fluoro-2-thiocytosine, 2-thiothymine, 4-thiothymine, 2,4-dithiothymine, and their nucleoside and nucleotide analogs), the mercapto-purines (e.g., 6-thioguanine, 8-thioadenine, 2-thioxanthine, 6-thioxanthine, 6-thiohypoxanthine, 6-thiopurine, and their nucleoside and nucleotide analogs), the thioethers (e.g., dimethylsulfide, diethylsulfide, diphenylsulfide, biotin), the disulfides (e.g., cystine, lipoic acid, diphenyl disulfide, iron disulfide, and 2-hydroxyethyldisulfide), the thiocarboxylic acids (e.g., thioacetic acid), the thioesters, the sulfonium salts (e.g., trimethylsulfonium or diphenylmethylsulfonium chloride), the sulfoxides (e.g., dimethylsulfoxide), the sulfones (e.g., dimethylsulfone), thioketones, thioamides, thiocyanates, isothiocyanates, thiocarbamates, dithiocarbamates, and trialkylphosphine sulfide (e.g., trioctylphosphine sulfide), thiourea compounds, or any of the inorganic sulfur-containing compounds, such as those enumerated above, which have been modified by inclusion of a hydrocarbon group. In particular embodiments, the organosulfur compound includes a sulfur-containing nucleic base (i.e., S-nucleobase), such as any of the mercapto-pyrimidines and mercapto-purines described above.

In a second embodiment, the microbial-mediated process includes a source of selenium. The source of selenium can be, for example, elemental selenium) ($Se^0$) or a selenium-containing compound. In one instance, the selenium-containing compound is an inorganic selenium-containing compound. Some examples of inorganic selenium-containing compounds include the inorganic selenates (e.g., $Na_2SeO_4$, $K_2SeO_4$, $MgSeO_4$, $(NH_4)_2SeO_4$, $H_2SeO_4$, or a metal selenate), the inorganic selenites (e.g., $Na_2SeO_3$, $H_2SeO_3$, or $(NH_4)_2SeO_3$), inorganic selenosulfates (e.g., $Na_2SSeO_3$ or $(NH_4)_2SSeO_3$), selenium dioxide, and selenium disulfide. In another instance, the selenium-containing compound is an organoselenium compound. The organoselenium compound contains at least one hydrocarbon group and is typically characterized by the presence of at least one selenium-carbon bond. Some examples of suitable organo selenium compounds include the hydrocarbon selenols (e.g., methaneselenol, ethaneselenol, n-propaneselenol, isopropaneselenol, and selenophenol (benzeneselenol)), the seleno-amino acids (e.g., selenocysteine, selenocystine, selenohomocysteine, selenomethionine), the selenopyrimidines (e.g., 2-selenouracil, 6-methyl-2-selenouracil, 4-selenouracil, 2,4-diselenouracil, 2-selenocytosine, 5-methyl-2-selenocytosine, 5-fluoro-2-selenocytosine, 2-selenothymine, 4-selenothymine, 2,4-diselenothymine, and their nucleoside and nucleotide analogs), the selenopurines (e.g., 6-selenoguanine, 8-selenoadenine, 2-selenoxanthine, 6-selenoxanthine, 6-selenohypoxanthine, 6-selenopurine, and their nucleoside and nucleotide analogs), the selenides (e.g., dimethylselenide, diethylselenide, and methylphenylselenide), the diselenides (e.g., dimethyldiselenide, diethyldiselenide, and diphenyldiselenide), the selenocarboxylic acids (e.g., selenoacetic acid, selenopropionic acid), the selenosulfides (e.g., dimethylselenosulfide), the selenoxides (e.g., dimethylselenoxide and diphenylselenoxide), the selenones, the selenonium salts (e.g., dimethylethylselenonium chloride), the vinylic selenides, selenopyrylium salts, trialkylphosphine selenide (e.g., trioctylphosphine selenide, i.e., TOPSe), selenourea compounds, or any of the inorganic selenium-containing compounds, such as those enumerated above, which have been modified by inclusion of a hydrocarbon group. In particular embodiments, the organoselenium compound includes a selenium-containing nucleic base (i.e., Se-nucleobase), such as any of the selenopyrimidines and selenopurines described above.

In a third embodiment, the microbial-mediated process includes a source of tellurium. The source of tellurium can be, for example, elemental tellurium) ($Te^0$) or a tellurium-containing compound. In one instance, the tellurium-containing compound is an inorganic tellurium-containing compound. Some examples of inorganic tellurium-containing compounds include the inorganic tellurates (e.g., $Na_2TeO_4$, $K_2TeO_4$, $MgTeO_4$, $(NH_4)_2TeO_4$, $H_2TeO_4$, $H_6TeO_6$, or a metal tellurate), the inorganic tellurites (e.g., $Na_2TeO_3$), and tellurium dioxide. In another instance, the tellurium-containing compound is an organotellurium compound. The organotellurium compound contains at least one hydrocarbon group and is typically characterized by the presence of at least one tellurium-carbon bond. Some examples of suitable organotellurium compounds include the hydrocarbon tellurols (e.g., methanetellurol, ethanetellurol, n-propanetellurol, isopropanetellurol, and tellurophenol (benzenetellurol)), the telluro-amino acids (e.g., tellurocysteine, tellurocystine, tellurohomocysteine, telluromethionine), the telluropyrimidines and their nucleoside and nucleotide analogs (e.g., 2-tellurouracil), the telluropurines and their nucleoside and nucleotide analogs, the tellurides (e.g., dimethyltelluride, diethyltelluride, and methylphenyltelluride), the ditellurides (e.g., dimethylditelluride, diethylditelluride, and diphenylditelluride), the telluroxides (e.g., dimethyltelluroxide and diphenyltelluroxide), the tellurones, the telluronium salts, the vinylic tellurides, telluropyrylium salts, tellurourea compounds, 24-telluracholestanol, or any of the inorganic tellurium-containing compounds, such as those enumerated above, which have been modified by inclusion of a hydrocarbon group. In particular embodiments, the organotellurium compound includes a tellurium-containing nucleic base (i.e., Te-nucleobase), such as any of the telluropyrimidines and telluropurines described above.

In a fourth embodiment, the microbial-mediated process includes a source of phosphorus. In one instance, the source of phosphorus is elemental phosphorus or an inorganic phosphorus-containing compound. Some examples of inorganic phosphorus-containing compounds include the inorganic phosphates (e.g., $Na_3PO_4$, $Na_2HPO_4$, $NaH_2PO_4$, $H_3PO_4$, $Mg_3(PO_4)_2$, or a transition metal phosphate), inorganic phosphites (e.g., $Na_3PO_3$, $Na_2HPO_3$, $NaH_2PO_3$, and $H_3PO_3$), and phosphorus oxides (e.g., $P_2O_3$ and $P_2O_5$). In another instance, the phosphorus-containing compound is an organophosphine compound. The organophosphine compound is characterized by the presence of at least one hydrocarbon group and at least one phosphorus atom. Some examples of suitable organophosphine compounds include the trialkylphosphines (e.g., triethylphosphine), the triarylphosphines (e.g., triphenylphosphine), organophosphites (e.g., triphenylphosphite), and organophosphates (e.g., triphenylphosphate).

In a fifth embodiment, the microbial-mediated process includes a source of arsenic. In one instance, the source of arsenic is elemental arsenic or an inorganic arsenic-containing compound. Some examples of inorganic arsenic-containing compounds include the inorganic arsenates (e.g., $Na_3AsO_4$, $Na_2HAsO_4$, $NaH_2AsO_4$, $H_3AsO_4$, $Mg_3(AsO_4)_2$, 1-arseno-3-phosphoglycerate, or a transition metal arsenate), inorganic arsenites (e.g., $Na_3AsO_3$, $Na_2HAsO_3$, $NaH_2AsO_3$, $H_3AsO_3$, $Ag_3AsO_3$, $Mg_3(AsO_3)_2$), arsenic oxides (e.g., $As_2O_3$ and $As_2O_5$), and arsenous carbonate (i.e., $As_2(CO_3)_3$). In another instance, the arsenic-containing compound is an organoarsine compound. The organoarsine compound is characterized by the presence of at least one hydrocarbon group and at least one arsenic atom. Some examples of suitable organoarsine compounds include the hydrocarbon arsines (e.g., trimethylarsine, triethylarsine, triphenylarsine, arsole, and 1,2-bis(dimethylarsino)benzene), arsenic-derivatized sugars (e.g., glucose 6-arsenate), arsonic acids (e.g., phenylarsonic acid, 4-aminophenylarsonic acid, 4-hydroxy-3-nitrobenzenearsonic acid, 2,3,4-trihydroxybutylarsonic acid, arsonoacetic acid, diphetarsone, diphenylarsinic acid, and 3-arsonopyruvate), arseno-amino acids and their derivatives (e.g., 3-arsonoalanine, arsenophenylglycine, and arsenate tyrosine), organoarsine oxides (e.g., methylarsine oxide, 4-aminophenylarsenoxide, oxophenylarsine, and oxophenarsine), 10,10'-oxybis-10H-phenoxarsine, 1-arseno-3-phosphoglycerate, arsenobetaine, arsenocholine, arsenotriglutathione, or any of the inorganic arsenic-containing compounds, such as those enumerated above, which have been modified by inclusion of a hydrocarbon group.

In a sixth embodiment, the microbial-mediated process includes a source of boron. The source of boron can be, for example, elemental boron, boric acid, a borate (e.g., borax, alkali and alkaline earth borates, and metal borates), a borate ester (e.g., sodium tetraethylborate), a diborate, a triborate, a tetraborate, a metaborate, a boron oxide, a boronic acid (e.g., phenylboronic acid), 2,4,6-triphenylborazine, boron citrate, or a boron cluster (e.g., decaborane).

In a seventh embodiment, the microbial-mediated process includes a source of aluminum. The source of aluminum can be, for example, aluminum hydroxide, aluminum oxide, aluminum acetate, aluminum sulfate, aluminum phenoxide, aluminum-2,4-pentanedionate, aluminum-2,2,6,6-tetramethyl-3,5-heptanedionate, or a metal aluminate.

In an eighth embodiment, the microbial-mediated process includes a source of gallium. The source of gallium can be, for example, gallium chloride, gallium nitrate, gallium citrate, gallium sulfate, gallium acetate, gallium hydroxide, a gallium oxide, a gallium sulfide, a gallium selenide, a gallium telluride, a gallium phosphide, gallium acetylacetonate, tris-(8-hydroxyquinoline) gallium(III), or a metal gallate (e.g., magnesium gallate).

In a ninth embodiment, the microbial-mediated process includes a source of indium. The source of indium can be, for example, indium chloride, indium nitrate, indium sulfate, indium acetate, indium acetylacetonate, an indium oxide, an indium sulfide, an indium selenide, an indium telluride, an indium phosphide, or indium nanoparticles.

In a tenth embodiment, the microbial-mediated process includes a source of silicon. The source of silicon can be, for example, silicic acid, a silicate, a siloxane (e.g., tetraethylorthosilicate and octamethyltrisiloxane), a cyclosiloxane (e.g., octamethylcyclotetrasiloxane), a silsesquioxane, a silicon oxide, or a silicon hydroxide.

In an eleventh embodiment, the microbial-mediated process includes a source of germanium. The source of germanium can be, for example, elemental germanium, germanium nitrate, a germanium oxide, a germanate, an organogermane (e.g., diphenyldimethylgermane), a germanium alkoxide (e.g., ethyltriethoxygermane), or 2-carboxyethylgermasesquioxane.

In a twelfth embodiment, the microbial-mediated process includes a source of tin. The source of tin can be, for example, elemental tin, stannic acid, a tin oxide, diacetoxy tin, bis-(triethyltin)oxide, bis-(triethyltin)sulfide, di-n-butyltinoxide, or dimethyl-bis(2,4-pentanedionate)tin.

Sources of numerous other elements can be similarly provided for use in a microbial-mediated process for producing precursor particles. For example, the oxides, sulfides, selenides, tellurides, hydroxides, halides, carboxylates, nitrates, or elemental nanoparticles are available for many other metals, such as antimony, bismuth, the transition metals, and the rare earth metals. Sources of nitrogen can be provided by, for example, an ammonium salt, nitrite, nitrate, or nitride compound.

Preferably, a reduced sulfide (e.g., $Na_2S$, $K_2S$, $H_2S$, or $(NH_4)_2S$), reduced selenide (e.g., $H_2Se$ or $(NH_4)_2Se$), reduced telluride (e.g., $H_2Te$ or $(NH_4)_2Te$), reduced phosphide, or reduced arsenide compound is not used in the microbial-mediated method described above. As known in the art, such reducing compounds have a propensity for precipitating various metals from solution. Since direct precipitation of the metals is to be avoided in the microbial-mediated process, such reducing compounds are preferably not included, or included only under conditions where an adverse reaction or precipitation does not occur.

The anaerobic microbes used in the microbial-mediated process are any microbes known in the art capable of forming particles, particularly nanoparticles, from one or more types of metal ions. The microbe can be, for example, a eukaryotic or procaryotic (and either unicellular or multicellular) type of microbe having this ability. Of particular relevance herein are the procaryotic organisms, which are predominantly unicellular, and are divided into two domains: the bacteria and the archaea. The microbes can be, in addition, fermentative, metal-reducing, dissimilatory, sulfate-reducing, thermophilic, mesophilic, psychrophilic, or psychrotolerant. The microbes are preferably those capable of directly reducing (i.e., without the use of chemical means) a sulfur-containing, selenium-containing, tellurium-containing, or arsenic-containing compound to, respectively, a sulfide (i.e., $S^{2-}$)-containing, selenide (i.e., $Se^{2-}$)-containing, telluride (i.e., $Te^{2-}$)-containing, or arsenide (i.e., $As^{3-}$)-containing compound, such as $H_2S$ or a salt thereof. In some embodiments, the microbes reduce the sulfur-, selenium-, tellurium-, or arsenic-containing compound without intermediate production of, respectively, elemental sulfur, selenium, tellurium, or arsenic. In other embodiments, the microbes reduce the sulfur-, selenium-, tellurium-, or arsenic-containing compound with intermediate production of, respectively, elemental sulfur, selenium, tellurium, or arsenic.

In one embodiment, the microbes used in the microbial-mediated process are thermophilic, i.e., those organisms capable of thriving at temperatures of at least about 40° C. (and more typically, at least 45° C. or 50° C.) and up to about 100° C. or higher temperatures. Preferably, the thermophilic microbes are either bacteria or archaea, and particularly, those possessing an active hydrogenase system linked to high energy electron carriers.

A group of thermophilic bacteria particularly considered for the microbial-mediated process are the species within the genus *Thermoanaerobacter*. A particular species of *Thermoanaerobacter* considered herein is *Thermoanaerobacter* strain TOR-39, a sample of which was deposited with the American Type Culture Collection (10801 University Blvd., Manassas, Va. 20010) on Sep. 7, 2001 as accession number PTA-3695. Strain TOR-39 is a thermophile that grows optimally at temperatures from about 65 to 80° C. The conditions needed to grow and maintain this strain, including basal medium, nutrients, vitamins, and trace elements are detailed in U.S. Pat. No. 6,444,453, the entire contents of which are incorporated herein by reference. Some particular strains of *Thermoanaerobacter ethanolicus* particularly considered herein include *T. ethanolicus* strain C1 and *T. ethanolicus* strain M1.

Another group of thermophilic bacteria particularly considered for the microbial-mediated process are the species within the class Thermococci. An order of Thermococci particularly considered herein is Thermococcales. A family of Thermococcales particularly considered herein is Thermococcaceae. A genus of Thermococcaceae particularly considered herein is *Thermococcus*. A species of *Thermococcus* particularly considered herein is *Thermococcus litoralis*.

Another group of thermophilic bacteria particularly considered for the microbial-mediated process are the species within the genus *Thermoterrabacterium*. A species of *Thermoterrabacterium* particularly considered herein is *Thermoterrabacterium ferrireducens*, and particularly, strain JW/AS-Y7.

Still another group of thermophilic bacteria particularly considered for the microbial-mediated process are the species within the phylum Deinococcus-Thermus. A class of Deinococcus-Thermus particularly considered herein is Deinococci. An order of Deinococci particularly considered herein is Thermales. A genus of Thermales particularly considered herein is *Thermus*. A species of *Thermus* particularly considered herein is *Thermus* sp. strain SA-01.

Other thermophilic bacteria particularly considered for the microbial-mediated process include thermophilic species within any of the genera *Thermoanaerobacterium* (e.g., *T. thermosulfurigenes*, *T. polysaccharolyticum*, *T. zeae*, *T. aciditolerans*, and *T. aotearoense*), *Bacillus* (e.g., *B. infernus*), *Clostridium* (e.g., *C. thermocellum*), *Anaerocellum* (e.g., *A. thermophilum*), *Dictyoglomus* (e.g., *D. thermophilum*), and *Caldicellulosiruptor* (e.g., *C. acetigenus*, *C. hydrothermalis*, *C. kristjanssonii*, *C. kronotskiensis*, *C. lactoaceticus*, *C. owensensis*, and *C. saccharolyticus*).

In another embodiment, the microbes considered for the microbial-mediated process are mesophilic (e.g., organisms thriving at moderate temperatures of about 15-40° C.) or psychrophilic (e.g., organisms thriving at less than 15° C.). As used herein, the term "psychrophilic" also includes "psychrotolerant". Psychrophilic bacteria are typically found in deep marine sediments, sea ice, Antarctic lakes, and tundra permafrost. Some examples of such microbes include species within the genera *Shewanella* (e.g., *S. alga* strain PV-1, *S. alga*, PV-4, *S. pealeana*, W3-7-1, *S. gelidimarina*, and *S. frigidimarina*), *Clostridium* (e.g., *C. frigoris*, *C. lacusfryxellense*, *C. bowmanii*, *C. psychrophilum*, *C. laramiense*, *C. estertheticum*, and *C. schirmacherense*), *Bacillus* (e.g., *B. psychrosaccharolyticus*, *B. insolitus*, *B. globisporus*, *B. psychrophilus*, *B. cereus*, *B. subtilis*, *B. circulans*, *B. pumilus*, *B. macerans*, *B. sphaericus*, *B. badius*, *B. licheniformis*, *B. firmus*, *B. globisporus*, and *B. marinus*), and *Geobacter* (e.g., *G. sulfurreducens*, *G. bemidjiensis*, and *G. psychrophilus*). Of particular interest are those strains capable of anaerobic growth with nitrate as an electron acceptor.

In yet another embodiment, the microbes considered for the microbial-mediated process are sulfur-reducing (e.g., sulfate- or sulfite-reducing) microbes. In a preferred embodiment, the sulfur-reducing microbes are one or more species selected from *Desulfovibrio* (e.g., *D. desulfuricans*, *D. gigas*, *D. salixigens*, and *D. vulgaris*), *Desulfolobus* (e.g., *D. sapovorans* and *D. propionicus*), *Desulfotomaculum* (e.g., *D. thermocisternum*, *D. thermobenzoicum*, *D. auripigmentum*, *D. nigrificans*, *D. orientis*, *D. acetoxidans*, *D. reducens*, and *D. ruminis*), *Desulfomicrobium* (e.g., *D. aestuarii*, *D. hypo-*

*geium*, and *D. salsuginis*), *Desulfomusa* (e.g., *D. hansenii*), *Thermodesulforhabdus* (e.g., *T. norvegica*) the order Desulfobacterales, and more particularly, the family Desulfobacteraceae, and more particularly, the genera *Desulfobacter* (e.g., *D. hydrogenophilus, D. postgatei, D. giganteus, D. halotolerans*, and *D. vibrioformis*), *Desulfobacterium* (e.g., *D. indolicum, D. anilini, D. autotrophicum, D. catecholicum, D. cetonicum, D. macestii, D. niacini, D. phenolicum, D. vacuolatum*), *Desulfobacula* (e.g., *D. toluolica* and *D. phenolica*), *Desulfobotulus* (*D. sapovorans* and *D. marinus*), *Desulfocella* (e.g., *D. halophilas*), *Desulfococcus* (e.g., *D. multivorans* and *D. biacutus*), *Desulfofaba* (e.g., *D. gelida* and *D. fastidiosa*), *Desulfofrigus* (e.g., *D. oceanense* and *D. fragile*), *Desulfonema* (e.g., *D. limicola, D. ishimotonii*, and *D. magnum*), *Desulfosarcina* (e.g., *D. variabilis, D. cetonica*, and *D. ovata*), *Desulfospira* (e.g., *D. joergensenii*), *Desulfotalea* (e.g., *D. psychrophila* and *D. arctica*), and *Desulfotignum* (*D. balticum, D. phosphitoxidans*, and *D. toluenicum*). Several of the sulfur-reducing microbes are either thermophilic or mesophilic. The sulfur-reducing microbes may also be psychrophilic or psychrotolerant.

In still other embodiments, the microbes considered for the microbial-mediated process are selenium-reducing (e.g., selenate-, selenite-, or elemental selenium-reducing), tellurium-reducing (e.g., tellurite-, tellurite-, or elemental tellurium-reducing), or arsenic-reducing (e.g., arsenate- or arsenite-reducing). In one embodiment, the selenium-, tellurium-, or arsenic-reducing microbe is one of the sulfur-reducing microbes described above. In another embodiment, the selenium- or tellurium-reducing microbe is selected from other microbes not described above, e.g., *Thauera selenatis, Sulfospirillum barnesii, Selenihalanerobacter shriftii, Bacillus selenitireducens, Pseudomonas stutzeri, Enterobacter hormaechei, Klebsiella pneumoniae*, and *Rhodobacter sphaeroides*. In yet another embodiment, the arsenic-reducing microbe is selected from any of the microbes described above, or in particular, from *Sulfurospirillum arsenophilum* or *Geospirillum arsenophilus*. It will also be appreciated that, in addition to the exemplary microorganisms listed above, other types of cultures, including mixed microbial cultures or uncharacterized microbial cultures from natural environments, and the like, may also be used in the invention. For example, cultures not yet characterized from natural hot springs where various metals are known to be present can demonstrate suitably high metal-reducing or selenium-reducing activity to carry out the inventive methods even though the exact species or genus of the microbes may be unknown and more than one species or genus may be present in said culture.

The microbes for the microbial-mediated process can also be dissimilatory iron-reducing bacteria. Such bacteria are widely distributed and include some species in at least the following genera: *Bacillus, Deferribacter, Desulfuromonas, Desulfuromusa, Ferrimonas, Geobacter, Geospirillum, Geovibrio, Pelobacter, Sulfolobus, Thermoanaerobacter, Thermoanaerobium, Thermoterrabacterium*, and *Thermus*.

The microbes used in the microbial-mediated process can be obtained and cultured by any of the methods known in the art. Some of the general processes by which such bacteria may be used are taught in U.S. Pat. Nos. 6,444,453 and 7,060,473, the entire disclosures of which are incorporated herein by reference. The isolation, culturing, and characterization of thermophilic bacteria are described in, for example, T. L. Kieft et al., "Dissimilatory Reduction of Fe(III) and Other Electron Acceptors by a *Thermus* Isolate," *Appl. and Env. Microbiology*, 65 (3), pp. 1214-21 (1999). The isolation, culture, and characterization of several psychrophilic bacteria are described in, for example, J. P. Bowman et al., "*Shewanella gelidimarina* sp. nov. and *Shewanella frigidimarina* sp. nov., Novel Antarctic Species with the Ability to Produce Eicosapentaenoic Acid (20:5ω3) and Grow Anaerobically by Dissimilatory Fe(III) Reduction," *Int. J. of Systematic Bacteriology* 47 (4), pp. 1040-47 (1997). The isolation, culture, and characterization of mesophilic bacteria are described in, for example, D. R. Lovley et al., "*Geobacter metallireducens* gen. nov. sp. nov., a microorganism capable of coupling the complete oxidation of organic compounds to the reduction of iron and other metals," *Arch. Microbiol.*, 159, pp. 336-44 (1993), the disclosure of which is incorporated herein by reference in its entirety.

The culture medium for sustaining the microbes can be any of the known aqueous-based media known in the art useful for this purpose. The culture medium may also facilitate growth of the microbes. As is well known in the art, the culture medium includes such components as nutrients, trace elements, vitamins, and other organic and inorganic compounds, useful for the sustainment or growth of microbes.

In the microbial-mediated process, the microbes are provided with at least one electron donor. An electron donor is any compound or material capable of being oxidatively consumed by the microbes such that donatable electrons are provided to the microbes by the consumption process. The produced electrons are used by the microbes to reduce one or more non-metal compounds and/or metal ions.

In one embodiment of the microbial-mediated process, the electron donor includes one or more carboxylate-containing compounds that can be oxidatively consumed by the microbes. Some examples of suitable carboxylate-containing compounds include formate, acetate, propionate, butyrate, oxalate, malonate, succinate, fumarate, glutarate, lactate, pyruvate, glyoxylate, glycolate, and citrate.

In another embodiment of the microbial-mediated process, the electron donor includes one or more sugars (i.e., saccharides, disaccharides, oligosaccharides, or polysaccharides) that can be oxidatively consumed by the microbes. Some examples of suitable sugars include glucose, fructose, sucrose, galactose, maltose, mannose, arabinose, xylose, lactose, and disaccharides therefrom, oligosaccharides therefrom, or polysaccharides therefrom.

In another embodiment of the microbial-mediated process, the electron donor includes one or more inorganic species that can be oxidatively consumed by the microbes. The inorganic species can be, for example, an oxidizable gas, such as hydrogen or methane. Such gases can be oxidized by hydrogen-consuming or methane-consuming microbes which have the capacity to reduce one or more metals or non-metal compounds by the produced electrons.

In the microbial-mediated process, the reaction components described above (i.e., anaerobic microbes, culture medium, metal components, and electron donor component) are combined in a suitable container and subjected to conditions (e.g., temperature, pH, and reaction time) suitable for producing the particles from the reaction components. In one embodiment, the container for holding the reaction components is simple by containing no more than container walls, a bottom, and a lid. In another embodiment, the container is more complex by including additional features, such as inlet and outlet elements for gases, liquids, or solids, one or more heating elements, nanoparticle separation features (e.g., traps or magnets), one or more agitating elements, fluid recirculating elements, electronic controls for controlling one or more of these or other conditions, and so on.

In some embodiments of the microbial-mediated process, the order of addition of components has essentially no bearing on the final compositional and physical characteristics of the produced particles. In other embodiments, the compositional and/or physical characteristics of the resulting particles are affected in some way by the order in which components are combined. For example, in some embodiments, it is preferable to first incubate a bacterial culture with a main group metal source (also referred to herein as a "non-metal source", such as any of the Group IV, V, and VI main group metals, such as, for example, a source of S, Se, Te, N, P, As, Sb, Si, and/or Ge) before introducing a metal source, wherein the metal can be, in particular, a reducible metal, and more particularly, a transition metal and/or an early main group metal, such as B, Al, Ga, In, Sn, or Pb. The foregoing embodiment is generally described by the particular embodiment depicted in the flow diagram shown in FIG. 1. In other embodiments, it is preferable to first incubate a bacterial culture before introducing both metal components. In yet other embodiments, it is preferable to incubate a bacterial culture in the presence of both metal components. Typically, the electron donor is included in the bacterial culture medium; however, the electron donor may be added during an enrichment step and/or during an incubation step.

Also shown in FIG. 1 are some optional steps of the microbial-mediated method, such as growing the bacterial culture by incubating the bacteria with only electron donor (enrichment step), and incubating the bacteria with a main group metal source and then addition of a transition metal. The growth step is particularly useful in culturing a bacterial source to process a transition metal or main group metal under conditions where such elements, at the concentrations used, would be excessively toxic to the bacteria. The growth process, thus, can be particularly useful in producing a bacterial population that can efficiently process an ordinarily toxic species (e.g., selenite, tellurate, arsenate, or other toxic metal species) in order to produce particles therefrom. An incubation step after addition of the metal is generally included, particularly when the metal needs to be reduced, such as in the production of CIGs nanoparticles wherein, typically, cupric ions are reduced to cuprous ions. Even when the reduction of a metal component is not needed, some incubation time is generally needed to permit crystal growth (during binding of components, e.g., $Cd^{+2}$ and dissolved hydrogen sulfide species) after adding the metal component.

In the microbial-mediated method, the combined components are subjected to conditions that induce the formation of particles therefrom. Some of the conditions that can affect formation of particles from the combined components include temperature, reaction time, precursor metal concentration, pH, and type of microbes used. In some embodiments, the reaction conditions may not require any special measures other than combining the reaction components at room temperature (e.g., 15-25° C.) and waiting for particles to grow over a period of time. In other embodiments, the combined reaction components are, for example, either heated, cooled, or modified in pH, in order to induce nanoparticle formation.

When thermophilic microbes are used in the microbial-mediated process, the temperature at which the reaction is conducted can preferably be at least, for example, 40° C., 45° C., 50° C., 55° C., 60° C., 65° C., 70° C., 75° C., 80° C., 85° C., or 90° C. depending on the type of thermophilic microbes being used. Any range resulting from any two of the foregoing values is also contemplated herein. When mesophilic microbes are used, the temperature can preferably be at least 15° C., 20° C., 25° C., or 30° C., and up to any of the temperatures given above for thermophilic microbes. When psychrophilic microbes are used, the temperature at which the reaction is conducted can preferably be less than, for example, 40° C., or at or less than 35° C., 30° C., 25° C., 20° C., 15° C., 10° C., 5° C., 0° C., or −5° C., or any range resulting from any two of the foregoing values. It is to be appreciated that, even though different exemplary temperatures have been given for each type of microbe, each type of microbe may be capable of thriving in temperatures well outside the typical temperatures given above. For example, a thermophilic microbe may also be capable of thriving to a useful extent at temperatures below 40° C. where mesophilic microbes traditionally thrive; or mesophilic or thermophilic microbes may be capable of thriving to a useful extent at temperatures below 15° C. (i.e., by being psychrotolerant in addition to mesophilic or thermophilic). Particularly when employing *Thermoanaerobacter* sp. strain TOR-39, the temperature is preferably maintained between about 45° C. and 75° C.

The reaction (incubation) time is the period of time that the combined reaction components are subjected to reaction conditions necessary for producing particles. The reaction time is very much dependent on the other conditions used, as well as the characteristics desired in the particles. For example, shorter reaction times (e.g., 1-60 minutes) may be used at elevated temperature conditions whereas longer reaction times (e.g., 1-7 days, or 1-3 weeks) may be used at lower temperatures to obtain a similar yield of product. Typically, shorter reaction times produce smaller particles than particles produced using longer reaction times under the same conditions. The incubation may be, for example, between 3 and 30 days, depending on the amount and size of the crystalline nanoparticle product desired.

The pH can also be suitably adjusted in the microbial-mediated process. Generally, when using thermophilic bacteria, the pH value is preferably within the range of 6.5-9. For example, particularly when employing *Thermoanaerobacter* sp. strain TOR-39, the pH is preferably maintained at a level between about 6.9 and 7.5. In different embodiments, depending on the microbe and other conditions, the pH is preferably acidic by being less than 7 (e.g., a pH of or less than 6.5, 6.0, 5.5, 5.0, 4.5, 4.0, 3.5, 3.0, 2.5, 2.0, 1.5, 1.0, or a range resulting from any two of these values), or preferably alkaline by being above 7 (e.g., a pH of or greater than 7.5, 8.0, 8.5, 9.0, 9.5, 10, 10.5, 11, 11.5, or a range resulting from any two of these values), or preferably approximately neutral by having a pH of about 7, e.g., 6.5-7.5.

In the microbial-mediated method, in addition to selecting reaction conditions (e.g., temperature, reaction time, and pH) on the basis of permitting or inducing the formation of nanoparticles, the reaction conditions can also be selected for numerous other purposes, including to modify or optimize the product yield, production efficiency, particle size or size range, particle composition or phase (e.g., crystalline vs. semicrystalline vs. amorphous), or particle morphology. For example, lower reaction temperatures may be employed to provide a more pure or single-crystalline product.

Once the particles are produced by the microbial-mediated process, they are isolated (i.e., separated) from the reaction components and byproducts formed by the reaction products. Any method known in the art for separation of particles from reaction components can be used herein.

In one embodiment of the microbial-mediated process, particles are separated from the reaction components by allowing the particles to settle to the bottom of the container and then decanting the liquid medium or filtering off the nanoparticle product. This settling may be accomplished with or without centrifugation. When centrifugation is used, the centrifugal (i.e., "g" force) causes settling of denser nanoparticles to the bottom or distal end of the spun containers. The collected particle product may be washed one or more times to further purify the product. The reaction container may optionally be fitted with a drain valve to allow the solid product to be removed without decanting the medium or breaking gas seals.

In another embodiment of the microbial-mediated process, the container in which the reaction components are housed is attached to (or includes) an external trap from which the particles can be removed. The trap is preferably in the form of a recess situated below flowing reaction solution. Particles in the flowing reaction solution are denser than the reaction solution, and hence, will settle down into the trap. The flowing reaction solution is preferably recirculated.

In another embodiment of the microbial-mediated process, a filter is used to trap the particles. The filter can be in the form of multiple filters that trap successively smaller particles. Depending on the particle size and other variables, one or more filters that trap the particles may contain a pore size of no more than about 0.5, 0.4, 0.3, 0.25, 0.2, 0.1, or 0.05 µm.

In yet another embodiment of the microbial-mediated process, in the case where the particles are magnetic, a magnetic source (e.g., electromagnet or other suitable magnetic field-producing device) can be employed to collect the particles. The magnetic source can be used as the sole means of separation, or used in combination with other separation means, such as a trap or filter.

In a particular set of embodiments of the microbial-mediated process, the general method described above is specifically directed to the preparation of particles (particularly, nanoparticles) having a CIGs-type composition according to the general formula (1) described above. The method generally includes: (a) subjecting a combination of reaction components to conditions conducive to microbially-mediated formation of the nanoparticles, wherein the combination of reaction components includes i) anaerobic microbes, ii) a culture medium suitable for sustaining the anaerobic microbes, iii) a metal component that includes Cu ions and at least one type of metal ion selected from In and Ga, iv) a main group metal component that includes at least one element selected from S, Se, and Te, and v) one or more electron donors that provide donatable electrons to the anaerobic microbes during consumption of the electron donor by the anaerobic microbes; and (b) isolating the particles.

In another particular set of embodiments of the microbial-mediated process, the general method described above is specifically directed to the production of particles (particularly, nanoparticles) having a kesterite-type composition according to the general formula (2) described above. The method generally includes: (a) subjecting a combination of reaction components to conditions conducive to microbially-mediated formation of the nanoparticles, wherein the combination of reaction components includes i) anaerobic microbes, ii) a culture medium suitable for sustaining the anaerobic microbes, iii) a chalcophile metal component that includes at least one chalcophile metal other than Sn, iv) a main group metal component that includes at least one nonmetal selected from S, Se, and Te, and v) one or more electron donors that provide donatable electrons to the anaerobic microbes during consumption of the electron donor by the anaerobic microbes; and (b) isolating the particles.

The microbial-mediated particle production process can be performed in a batchwise manner or in a continuous manner. Examples of suitable arrangements for performing the method of the invention in a batchwise or continuous manner are described in U.S. Pat. No. 6,444,453, all of which is incorporated by reference herein, as particularly shown and described by FIGS. 3 and 4 and Example 6 therein. Because the nanoparticles tend to grow larger the longer they remain in the culture, continuous collection of nanoparticle product from a recirculating fluid may be used as a means of controlling particle size. In addition, the degree of fluid circulation (e.g., flow rate) can be modulated to promote shedding of the nanoparticles from the microbes.

In another aspect, the invention is directed to an apparatus for producing the films described herein. The apparatus includes at least a deposition device for depositing a layer of the particles onto a substrate. In embodiments where the layer of particles is heated, a non-pulse or pulse thermal processing device is also included. In particular embodiments, the deposition device and thermal processing device are integrated. By being integrated, the deposition and thermal processing devices are within close enough proximity that a layer of precursor particles can be produced and conveniently transferred to the thermal processing device in a short period of time (for example, within a few minutes or seconds). For example, the apparatus may include an ink-jet device coupled to or integrated with a non-pulsed or pulsed thermal processing station. In some embodiments, the deposition and thermal processing devices are connected or reversibly attached. In further embodiments, the deposition and thermal processing devices share, or are commonly connected to, one or more apparatus elements (such as a stand or platform on which the substrate is placed, or a common housing) for added integration and ease of use. For even further ease of use, the apparatus may be a single reconfigurable unit with one or more detachable or movable components that allow the unit to be reconfigured from a particle deposition mode to a thermal treatment mode, and vice-versa.

In yet further embodiments, the above apparatus can also be integrated with a particle preparation unit. By being integrated, the particle preparation unit (e.g., a microbial-mediated apparatus described above) is in close enough proximity to the particle deposition unit (e.g., an ink-jet printer or sono-spray unit) such that particles prepared in the particle preparation unit can be conveniently transferred to the particle deposition unit in a short period of time. In some embodiments, the particle preparation and deposition units are connected or reversibly attached. For example, in particular embodiments, the particle preparation and deposition units are connected by a conduit that transfers particles suspended in a liquid medium, as produced in the particle preparation unit, to the particle deposition unit. One or more intermediary units, such as a particle isolation, particle washing, and/or particle suspension or mixing station, may be connected between the particle preparation and deposition units, or integrated within the particle preparation unit.

In further aspects, the invention is directed to large-scale automated production of films. The integrated apparatus described above would be a significant benefit in furthering such large-scale production. In particular embodiments, films are produced on a large scale, using methods described herein, integrated into a roll-to-roll processing system, such as any of the roll-to-roll processing systems well-known in the art. The roll-to-roll processing system considered herein utilizes a flexible plastic, polymeric material, or metal as the roll substrate (or foil). The roll-to-roll processing equipment can be integrated with one or more of the pulse thermal processing, particle deposition, and particle preparation units described above. Roll-to-roll processing is particularly useful in producing thin-film solar cells, large-area flexible displays, and flexible electronics.

In some embodiments, lithographic (particularly photolithographic) methods known in the art are combined with the film production methods described herein. For example, particles may be produced by any of the methods described herein and deposited onto a substrate in a patterned form by employing spraying methods in combination with conventional lithographic methods. In other embodiments, particles are deposited on a substrate without lithographic means, and then converted to a patterned film by subjecting the layer of particles to a thermal pulse that has been modified, by lithographic means, to produce the pattern. In yet other embodiments, the film, as produced by methods described herein, is subjected to one or more lithographic steps to modify (e.g., pattern) the film. In still other embodiments, one or more films in a multilayer structure are produced by conventional lithographic means, while one or more of the films are produced by the methods described herein.

In some embodiments, dispersion methods known in the art are combined with the film production methods described herein. Many chemicals can be used for the chemical dispersion of these aggregates. Some examples of useful dispersion chemicals include 2-mercaptoethanol, nitrilotriacetic acid, oleic acid, sodium oleate, polyethylene glycol, polyethylenimine, perfluoromethylcyclohexane, sodium dodecyl sulfate, a polysorbate (e.g., the Tween® surfactants, such as Tween® 20), trifluoroacetic acid, and thioglycerol. In particular, nitrilotriacetic acid (NTA) can enhance the dispersion of particle aggregates. For example, treatment with NTA has been shown to reduce the average size of CIGs particles from 37 microns (in aggregated form) to about 300 nm (much less aggregated form). Further treatments with ultrasonication can continue to reduce the particle size to about 90 nm, which is approaching the primary particle size (50-75 nm per XRD analysis). These chemically-dispersed CIGs nanoparticles can advantageously disperse and suspend well during deposition, and advantageously provide crack-free thin films.

EXAMPLE 1

Synthesis of CIGs Particles

Into a pre-incubated culture bottle including only electron donor and *Thermoanaerobacter* strain TOR-39 in the biological medium, 5 mM of selenite was dosed and then 0.1 mM of metal precursor $Cu_{0.55}In_{0.4}Ga_{0.6}$ ratio (based on concentration sum of indium and gallium) was dosed consecutively for 10 days. Harvested samples after the scheduled incubation were washed and centrifuged with deionized water more than five times. The final product had a measured Cu/(Ga+In) ratio between 0.798-0.896 and Ga/(Ga+In) ratio between 0.292-0.320. The final composition can be expressed as $Cu_{0.88}In_{0.72}Ga_{0.32}Se_2$.

EXAMPLE 2

Characterization of CIGs Particles

Figure 3:
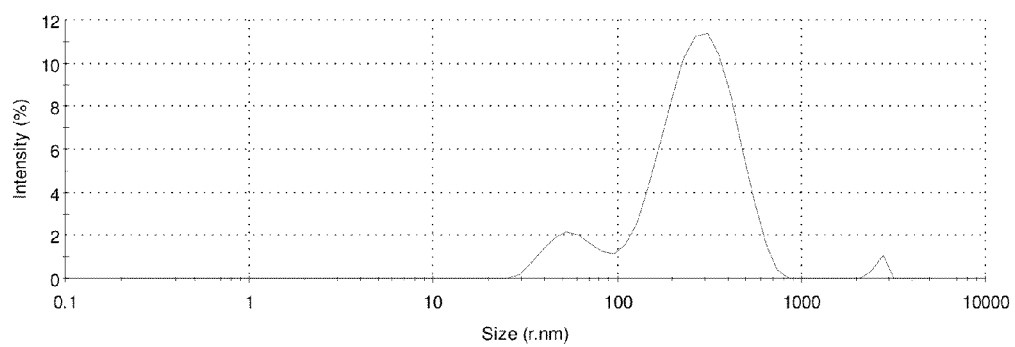
FIG. 3. Graph showing size distribution of the CIGs particles of FIG. 2 treated by nitrilotriacetic acid (particle size reduced to about 300 nm).
Figure 4:
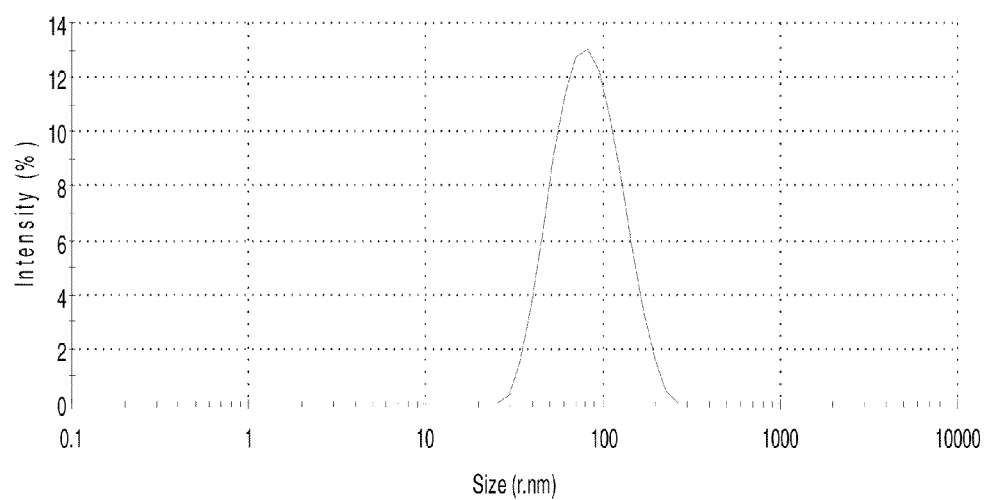
FIG. 4. Graph showing size distribution of the CIGs particles of FIG. 2 treated by nitrilotriacetic acid and ultrasonication (further size reduction to about 90 nm).
Figure 5:
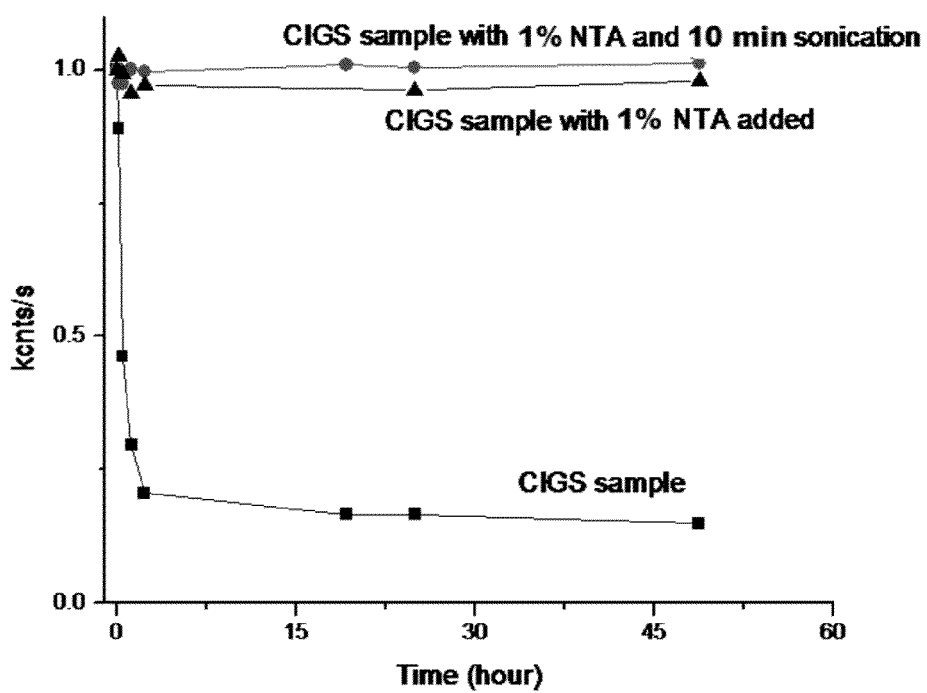
FIG. 5. Graph showing sedimentation behavior of CIGs particle suspensions before and after chemical dispersing treatment, as measured by dynamic light scattering. Kcnts/s is the scattering intensity from particles, which decrease with the particle settlement.
Figure 6:
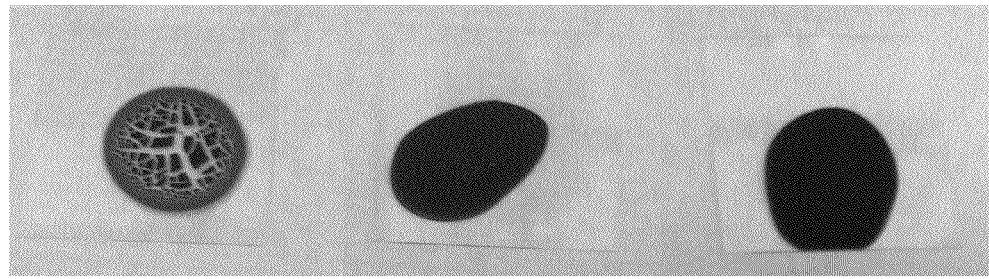
FIG. 6. Drop-casting films made using the as-synthesized CIGs particles (left), and using the dispersant-treated CIGs particles (middle: 1% NTA; right: 4% NTA).

As shown in FIG. 2, the as-synthesized CIGs exhibited agglomerated particles with average size of about 37 μm. It has been found herein that nitriloacetic acid (NTA) significantly improved the dispersion of particle aggregates. The size distribution of CIGs after the treatment of NTA reduced from 37 μm to about 300 nm (FIG. 3). Further treatments with ultrasonication further reduced the particle size to about 90 nm (FIG. 4), which approaches the primary particle size (i.e., approximately 50-75 nm per XRD analysis). These chemically dispersed CIGs nanoparticles dispersed and suspend well while the non-treated CIGs suspension quickly sedimented (FIG. 5).

EXAMPLE 3

Precursor Film Formation

Films were deposited from solution using drop-cast deposition method, (or spin coating method, or sono-spray deposition). 100 μL of CIGs nanoparticle solution with NTA concentration (as described earlier) were deposited onto a glass or Mo-coated glass substrate with a micro pipette. Films were set to dry via one of two methods: set on hot plate for 15 minutes at 65° C., or dried in air in a fume hood for two hours. Significantly, the films made using the post-treated CIGs nanoparticles were crack-free (FIG. 5).

EXAMPLE 4

Pulsed Thermal Method for Conversion of Precursor Film into Coalesced Film

Figure 7:
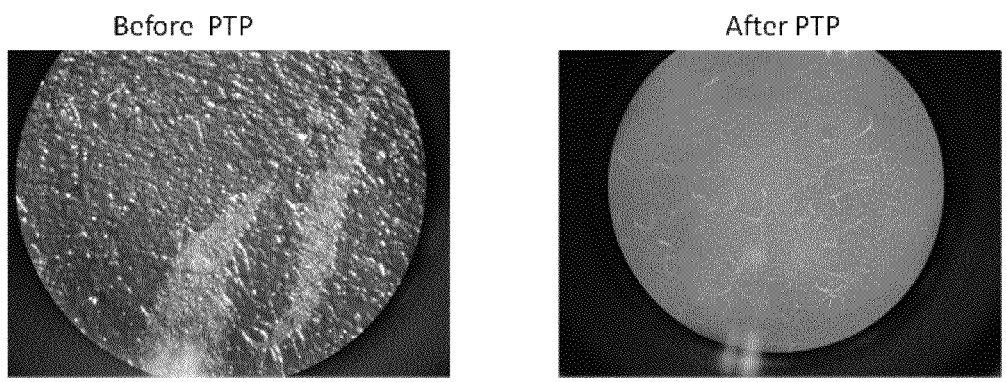
FIG. 7. Films before and after pulse thermal processing of the precursor film.

CIGs nanoparticle precursor films on Mo-coated glass were processed via pulsed thermal processing method. The films were placed in an environmental chamber (protects from out-gassing) with quartz window. In some of the runs, argon gas was used as the ambient atmosphere inside the environmental chamber. The samples were placed under lamp and pulsed one time at a radiant peak power in the range of 1.8-12 kW/cm² and at a pulse time in the range of 700-2100 microseconds (process space included a variation in energy exposure and in pulse time). FIG. 7 shows films before and after thermal processing.

While there have been shown and described what are at present considered the preferred embodiments of the invention, those skilled in the art may make various changes and modifications which remain within the scope of the invention defined by the appended claims.

What is claimed is:
1. A method for producing a film, the method comprising:
 (i) producing precursor particles from microbes, wherein said precursor particles have a size of up to 100 microns and a composition comprising at least one element selected from S, Se, and Te and at least two elements selected from Cu, Fe, Zn, Sn, Cd, In, Ga, and Al;
 (ii) disposing said precursor particles on a substrate to form a layer of said precursor particles on said substrate; and
 (iii) melting said layer of precursor particles on said substrate until at least a portion of the melted particles are planarized and merged in said film.
2. The method of claim 1, wherein said film is continuous.
3. The method of claim 1, wherein said method further comprises depositing at least a second film over said film to produce a multilayer structure, wherein the at least two overlaid films are different in composition or structure.
4. The method of claim 1, wherein said precursor particles have a composition that exhibits a photovoltaic property.
5. The method of claim 1, wherein said precursor particles have a composition according to the formula:

$$Cu(In_xGa_{1-x})X_2 \qquad (1)$$

wherein x is an integral or non-integral numerical value of or greater than 0 and less than or equal to 1, X represents at least one element selected from S, Se, and Te, and the relative molar ratio of Cu can diverge from 1.
6. The method of claim 1, wherein said precursor particles have a kesterite-type composition according to the formula:

$$M_3SnX_4 \qquad (2)$$

wherein M represents at least one chalcophile metal other than Sn, and X represents at least one element selected from S, Se, and Te.

7. The method of claim 1, wherein said method further comprises adjusting the stoichiometric ratio of elements in the film by a corresponding adjustment in the stoichiometric ratio of elements in the precursor particles.

8. The method of claim 1, wherein said melting is achieved by subjecting said layer of precursor particles to a pulse of thermal energy having an intensity and duration of time effective for melting at least a portion of said precursor particles to produce said film.

9. The method of claim 8, wherein the pulse has a duration of up to 1 second.

10. The method of claim 1, wherein said film possesses a degree of porosity.

11. The method of claim 10, wherein said degree of porosity is adjusted by adjusting the duration of time of said pulse of thermal energy.

12. The method of claim 1, wherein said layer of precursor particles is formed by spraying a liquid suspension of said precursor particles on said substrate.

13. The method of claim 12, wherein said spraying is provided by sonospraying.

14. The method of claim 12, wherein said spraying is provided by inkjet spraying.

15. A method for producing a pattern on a substrate, the method comprising subjecting a select portion of a layer of precursor particles to a pattern-wise pulse of thermal energy that pattern-wise melts said select portion of precursor particles to an extent that the melted particles are planarized and merged in the portion of said layer subjected to said pulse to produce said pattern in said layer, followed by removal of precursor particles not exposed to said pattern-wise pulse of thermal energy, wherein said pattern-wise pulse of thermal energy is produced by patterning said pulse of thermal energy with a patterned mask, and wherein said layer of precursor particles is produced by (i) producing precursor particles from microbes, wherein said precursor particles have a size of up to 100 microns and a composition comprising at least one element selected from S, Se, and Te and at least two elements selected from Cu, Fe, Zn, Sn, Cd, In, Ga, and Al; and (ii) disposing said precursor particles on said substrate to form said layer of said precursor particles.

16. A method for producing a pattern on a substrate, the method comprising producing a patterned layer of precursor particles, and melting said precursor particles until the melted particles are planarized and merged, wherein said precursor particles are produced from microbes and have a size of up to 100 microns and a composition comprising at least one element selected from 5, Se, and Te and at least two elements selected from Cu, Fe, Zn, Sn, Cd, In, Ga, and Al.

17. The method of claim 16, wherein said patterned layer of precursor particles is produced by ink-jet printing of said precursor particles to form a pattern of said precursor particles.

18. The method of claim 17, wherein said ink-jet printing pattern-wise deposits at least two different types of particles in separate regions of the patterned layer.

19. A method for producing a multilayer structure, the method comprising:
(i) subjecting a select portion of a first layer of precursor particles to a pattern-wise pulse of thermal energy that pattern-wise melts said select portion of precursor particles to an extent that the melted particles are planarized and merged in the portion of said first layer subjected to said pulse to produce a pattern in said first layer, followed by removal of precursor particles not exposed to said pattern-wise pulse of thermal energy, wherein said pattern-wise pulse of thermal energy is produced by patterning said pulse of thermal energy with a patterned mask;
(ii) depositing a second layer of precursor particles on said first layer; and
(iii) subjecting at least a portion of said second layer of precursor particles to a pulse of thermal energy to melt at least a portion of said second layer of precursor particles to an extent that the melted particles are planarized and merged;
wherein the precursor particles in at least one of the first or second layer of precursor particles are produced from microbes and have a size of up to 100 microns and a composition comprising at least one element selected from S, Se, and Te and at least two elements selected from Cu, Fe, Zn, Sn, Cd, In, Ga, and Al.

20. A method for producing a multilayer structure, the method comprising:
(i) producing a patterned layer of precursor particles, by ink-jet printing of said precursor particles;
(ii) melting said patterned layer of precursor particles until the melted particles are planarized and merged to form a patterned first layer;
(iii) depositing a second layer of precursor particles on said patterned first layer; and
(iv) subjecting at least a portion of said second layer of precursor particles to a pulse of thermal energy to melt at least a portion of said second layer of precursor particles to an extent that the melted particles are planarized and merged;
wherein the precursor particles in at least one of the first or second layer of precursor particles are produced from microbes and have a size of up to 100 microns and a composition comprising at least one element selected from S, Se, and Te and at least two elements selected from Cu, Fe, Zn, Sn, Cd, In, Ga, and Al.

* * * * *